US007067554B2

(12) United States Patent
Mjalli et al.

(10) Patent No.: US 7,067,554 B2
(45) Date of Patent: Jun. 27, 2006

(54) METHOD FOR THE SYNTHESIS OF COMPOUNDS OF FORMULA I AND THEIR USES THEREOF

(75) Inventors: Adnan M. M. Mjalli, Jamestown, NC (US); Ramesh Gopalaswamy, Greensboro, NC (US); Kwasi A. Avor, High Point, NC (US); Christopher L. Wysong, Ashland, KY (US); Patron Andrew, Encinitas, CA (US)

(73) Assignee: TransTech Pharma, Inc., High Point, NC (US)

( * ) Notice: Subject to any disclaimer, the term of this patent is extended or adjusted under 35 U.S.C. 154(b) by 45 days.

(21) Appl. No.: 10/611,741

(22) Filed: Jul. 1, 2003

(65) Prior Publication Data
US 2004/0097407 A1 May 20, 2004

Related U.S. Application Data

(62) Division of application No. 09/799,317, filed on Mar. 5, 2001, now Pat. No. 6,613,801.

(60) Provisional application No. 60/207,343, filed on May 30, 2000.

(51) Int. Cl.
*A61K 31/21* (2006.01)
*C07C 233/00* (2006.01)
(52) U.S. Cl. ........................ 514/514; 514/516; 564/155
(58) Field of Classification Search ................ 564/155; 514/514, 516
See application file for complete search history.

(56) References Cited

U.S. PATENT DOCUMENTS

| 4,166,452 | A | 9/1979 | Generales, Jr. |
| 4,265,874 | A | 5/1981 | Bonsen et al. |
| 4,356,108 | A | 10/1982 | Schwab et al. |
| 4,873,313 | A | 10/1989 | Crawford et al. |
| 4,963,539 | A | 10/1990 | Delaney |
| 5,202,424 | A | 4/1993 | Vlassara et al. |
| 5,585,344 | A | 12/1996 | Vlassara et al. |
| 5,688,653 | A | 11/1997 | Ulrich et al. |
| 5,864,018 | A | 1/1999 | Morser et al. |
| 5,922,770 | A | 7/1999 | Peschke et al. |
| 5,939,526 | A | 8/1999 | Gaugler et al. |
| 6,100,098 | A | 8/2000 | Newkirk |
| 6,613,801 | B1 * | 9/2003 | Mjalli et al. ................. 514/514 |

FOREIGN PATENT DOCUMENTS

| GB | 2 005 674 | 4/1979 |
| WO | WO 95/09838 | 4/1995 |
| WO | WO 95/35279 | 12/1995 |
| WO | WO 96/32385 | 10/1996 |
| WO | WO 97/22618 | 6/1997 |
| WO | WO 97/26913 | 7/1997 |
| WO | WO 97/39121 | 10/1997 |
| WO | WO 9739125 | 10/1997 |
| WO | WO 98/22138 | 5/1998 |
| WO | WO 98/33492 | 8/1998 |
| WO | WO 99/07402 | 2/1999 |
| WO | WO 99/18987 | 4/1999 |
| WO | WO 99/25690 | 5/1999 |
| WO | WO 99/50230 | 10/1999 |
| WO | WO 99/54485 | 10/1999 |
| WO | WO 00/20458 | 4/2000 |
| WO | WO 00/20621 | 4/2000 |

OTHER PUBLICATIONS

Albercio, F. & Carpino, L.A., "Coupling Reagents and Activation" *Methods in Enzymology* 289:104-126, Academic Press, San Diego (1997).
Barton, J.W., "In Protection of N-H Bonds and $NR_3$", *Protective Groups in Organic Chemistry*, J.F.W. McOmie, ED., Plenum Press, New York, NY (1973).
Berge, S.M., et al., "Pharmaceutical Salts" *Journal of Pharmaceutical Sciences* 66:1-19 (1977).
Chitaley, K., et al., "Antagonism of Rho-Kinase Stimulates Rate Penile Erection via a Nitric Oxide-Independent Pathway" *Nature Medicine* 7:119-122 (2002).
Degenhardt, T.P., et al., "Chemical Modification of Proteins by Methylglyoxal" *Cell Mol. Biol.*, 44:1139-1145 (1998).
Dyer, D.G., et al., "Accumulation of Maillard Reaction Products in Skin Collagen in Diabetes and Aging" *J. Clin. Invest.*, 91:2463-2469 (1993).
Dyer, D.G., et al., "Formation of Pentosidine during Nonenzymatic Browning of Proteins by Glucose" *J. Biol. Chem.*, 266:11654-11660 (1991).
Greene, T.W., "Protection for the Amino Group" *Protective Groups in Organic Synthesis*, John Wiley and Sons, New York, NY, Chapter 7 (1981).
Hammes, H.P., et al., "Diabetic Retinopathy Risk Correlates with Intracellular Concentrations of the Glycoxidation Product $N^\epsilon$-(Carboxymethyl) Lysine Independently of Glycohaemoglobin Concentrations" Diabetologia, 42:603-607 (1999).

(Continued)

*Primary Examiner*—Barbara P. Badio
(74) *Attorney, Agent, or Firm*—Kilpatrick Stockton

(57) ABSTRACT

This invention provides certain compounds, methods of their preparation, pharmaceutical compositions comprising the compounds, their use in treating human or animal disorders. The compounds of the invention are useful as modulators of the interaction between the receptor for advanced glycated end products (RAGE) and its ligands, such as advanced glycated end products (AGEs), S100/calgranulin/EN-RAGE, β-amyloid and amphoterin, and for the management, treatment, control, or as an adjunct treatment for diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

7 Claims, No Drawings

OTHER PUBLICATIONS

Hoffman, M.A., et al., "RAGE Mediates a Novel Proinflammatory Axis: A Central Cell Surface Receptor for S100/Calgranulin Polypeptides" *Cell*, 97:889-901 (1999).

Hori, O., et al., "The Receptor for Advanced Glycation End Products (RAGE) Is a Cellular Binding site for Amphoterin" *J. Biol. Chem.*, 270:25752-761 (1995).

Huttunen, H.J., et al., "Receptor for Advanced Glycation End Products (RAGE)-Mediated Neurite Outgrowth and Activation of NF-Kappa B Require the Cytoplasmic Domain of the Receptor But Different Downstream Signaling Pathways" *J. Biol. Chem.* 274(28):19919-24 (1999).

Kumar, S.R., et al., "RAGE at the Blood-Brain Barrier Mediates Neurovascular Dysfunction Caused by Amyloid$\beta_{1-40}$ Peptide" *Neurosci. Program*, 141-#255.19 (2000).

Leder, A. et al., "v-HA-ras Transgene Abrogates the Initiation Step in Mouse Skin Tumorigenesis: Effects of Phorbol Esters and Retinoic Acid" *Proc. Natl. Acad. Sci., USA*, 87:9178-9182 (1990).

Li, J. et al., "Sp1-Binding elements In the Promoter of RAG Are Essential for Amphoterin-Mediated Gene Expression in Cultured Neuroblastoma Cells." *J. Biol. Chem.*, 273:30870-30878 (1998).

Li, J. et al., "Characterization and Functional Analysis of the Promoter of RAGE, the Receptor for Advanced Glycation End Products," *J. Biol. Chem.*, 272:16498-16506 (1997).

Lugering, N. et al., "The Myeloic Related Protein MRP8/14 (27E10 Antigen)—Usefulness as a Potential Marker for Disease Activity in Ulcerative Colitis and Putative Biological Function" Eur. J. Clin. Invest., 25:659-664 (1995).

Miyata, T. et al., "$\beta_2$-Microglobulin Modified with Advanced Glycation End Products Is a Major Component of Hemodialysis-Associated Amyloidosis" *J. Clin. Invest.*, 92:1243-1252 (1993).

Miyata, T. et al., "*The Receptor for Advanced Glycation End Products* (RAGE) Is a Central Mediator of the Interaction of AGE-$\beta_2$Microglobulin with Human Mononuclear Phagocytes Via an Oxidant-Sensitive Pathway" *J. Clin. Invest.*, 98:1088-1094 (1996).

Neeper, M., et al., "Cloning and Expression of a Cell Surface Receptor for Advanced Glycosylation End Products of Proteins" *J. Biol. Chem.*, 267:14998-15004 (1992).

Parkkinen, J. et al., "Amphoterin, the 30-kDa Protein in a Family of HMG1-Type Polypeptides" *J. Biol Chem.*, 268:19726-19738 (1993).

Rammes, A. et al., Myeloid-Related Protein (MRP) 8 and MRP 14, Calcium-Binding Proteins of the S100 Family, Are Secreted by Activated Monocytes via a Novel, Tubulin-Dependent Pathway *J. Biol. Chem.*, 272:9496-9502 (1997).

Rauvala, H. et al., "Isolation and Some Characteristics of an Adhesive Factor of Brain That Enhances Neurite Outgrowth In Central Neurons" *J. Biol. Chem.*, 262:16625-16635 (1987).

Reddy, S. et al., "Nε-(Carboxymethyl) Lysine Is a Dominant Advanced Glycation End Product (AGE) Antigen in Tissue Proteins" *Biochem.*, 34:10872-10878 (1995).

Schafer, B.W., et al., "The S100 Family of EF-Hand Calcium-Binding Proteins: Functions and Pathology" *TIBS*, 21:134-140 (1996).

Schleicher, E.D., et al., "Increased Accumulation of the Glycoxidation Product Nε-(Carboxymethyl) Lysine in Human Tissues In Diabetes and Aging" *J. Clin. Invest.*, 99(3):457-468 (1997).

Schmidt, A.M. et al., "The Dark Side of Glucose" *Nature Med.*, 1:1002-1004 (1995).

Schmidt, A.M., et al., "The V-Domain of Receptor for Advanced Glycation Endproducts (RAGE) Mediates Binding of AGEs: A Novel Target for Therapy of Diabetic Complications:" *Supplement to Circulation* vol. 96, #194 (1997).

Taguchi, A. et al., "Blockade of RAGE—Amphoterin Signalling Suppresses Tumour Growth and Metastases" *Nature*, 405:354-360 (2000).

Tanaka, N., et al., "The Receptor for Advanced Glycation End Products Is Induced by the Glycation Products Themselves and Tumor Necrosis Factor-α through Nuclear Factor-κB, and by 17 β-Estradoil through Sp-1 in Human Vascular Endothelial Cells" *J. Biol. Chem.*, 275:25781-25790 (2000).

Teillet et al., "Food Restriction Prevents Advanced Glycation End Product Accumulation and Retards Kidney Aging in Lean Rats" *J. Am. Soc. Nephrol.*, 11:1488-1497 (2000).

Vlassara, H., "Advanced Glycation End-Products and Atherosclerosis" *The Finnish Medical Society DUODECIM, Ann. Med.*, 28:419-426 (1996).

Wautier et al., "Receptor-Mediated Endothelial Cell Dysfunction In Diabetic Vasculopathy: Soluble Receptor for Advanced Glycation End Products Blocks Hyperpermeability in Diabetic Rats" *J. Clin. Invest.*, 97:238-243 (1996).

Yan, S.-D., et al., "RAGE and Amyloid-β Peptide Neurotoxicity in Alzheimer's Disease" *Nature* 382:685-691 (1996).

Yan, S.-D., et al., "An Intracellular Protein That Binds Amyloid-β Peptide and Mediates Neurotoxicity in Alzheimer's Disease" *Nature*, 389:689-695, (1997).

Yan, S.-D. et al., "Amyloid-β Peptide—Receptor for Advanced Glycation Endproduct Interaction Elicits Neuronal Expression of Macrophage-Colony Stimulating Factor: A Proinflammatory Pathway in Alzheimer Disease" *Proc. Natl. Acad. Sci., USA*, 94:5296-5301 (1997).

Yan, S.-D. et al., "Receptor-Dependent Cell Stress and Amyloid Accumulation in Systemic Amyloidosis" *Nat. Med.* 6:643-651 (2000).

Yan, S.-D. et al., "Enhanced Celllular Oxidant Stress by the Interaction of Advanced Glycation Endproducts With Their Receptors Binding Proteins" J. Biol. Chem. 269:9889-9897 (1994).

Zimmer, D. et al., The S100 Protein Family: History, Function, and Expression *Brain Res. Bull*, 37:417-429 (1995).

International Search Report for PCT/US 01/17251 dated Aug. 14, 2001.

* cited by examiner

METHOD FOR THE SYNTHESIS OF COMPOUNDS OF FORMULA I AND THEIR USES THEREOF

This application is a divisional application of application Ser. No. 09/799,317, filed Mar. 5, 2001, now U.S. Pat. No. 6,613,801, which claims the benefit of U.S. Provisional Application No. 60/207,343, filed May 30, 2000.

FIELD OF THE INVENTION

This invention relates to compounds which are modulators of the receptor for advanced glycated end products (RAGE) and interaction with its ligands such as advanced glycated end products (AGEs), S100/calgranulin/EN-RAGE, β-amyloid and amphoterin, for the management, treatment, control, or as an adjunct treatment of diseases caused by RAGE.

BACKGROUND OF THE INVENTION

Incubation of proteins or lipids with aldose sugars results in nonenzymatic glycation and oxidation of amino groups on proteins to form Amadori adducts. Over time, the adducts undergo additional rearrangements, dehydrations, and cross-linking with other proteins to form complexes known as Advanced Glycosylation End Products (AGEs). Factors which promote formation of AGEs included delayed protein turnover (e.g. as in amyloidoses), accumulation of macromolecules having high lysine content, and high blood glucose levels (e.g. as in diabetes) (Hori et al., *J. Biol. Chem.* 270: 25752–761, (1995)). AGEs have implicated in a variety of disorders including complications associated with diabetes and normal aging.

AGEs display specific and saturable binding to cell surface receptors on endothelial cells of the microvasculature, monocytes and macrophages, smooth muscle cells, mesengial cells, and neurons. The Receptor for Advanced Glycated End products (RAGE) is a member of the immunoglobulin super family of cell surface molecules. The extracellular (N-terminal) domain of RAGE includes three immunoglobulin-type regions, one V (variable) type domain followed by two C-type (constant) domains (Neeper et al., *J. Biol. Chem.* 267:14998–15004 (1992). A single transmembrane spanning domain and a short, highly charged cytosolic tail follow the extracellular domain. The N-terminal, extracellular domain can be isolated by proteolysis of RAGE to generate soluble RAGE (sRAGE) comprised of the V and C domains.

RAGE is expressed in most tissues, and in particular, is found in cortical neurons during embryogenesis (Hori et al., *J. Biol. Chem.* 270:25752–761 (1995)). Increased levels of RAGE are also found in aging tissues (Schleicher et al., *J. Clin. Invest.* 99 (3): 457–468 (1997)), and the diabetic retina, vasculature and kidney (Schmidt et al., *Nature Med.* 1:1002–1004 (1995)). Activation of RAGE in different tissues and organs leads to a number of pathophysiological consequences. RAGE has been implicated in a variety of conditions including: acute and chronic inflammation (Hofmann et al., *Cell* 97:889–901 (1999)), the development of diabetic late complications such as increased vascular permeability (Wautier et al., *J. Clin. Invest.* 97:238–243 (1995)), nephropathy (Teillet et al., *J. Am. Soc. Nephrol.* 11:1488–1497 (2000)), atherosclerosis (Vlassara et. al., *The Finnish Medical Society DUODECIM, Ann. Med.* 28:419–426 (1996)), and retinopathy (Hammes et al., *Diabetologia* 42:603–607 (1999)). RAGE has also been implicated in Alzheimer's disease (Yan et al., *Nature* 382: 685–691, (1996)), erectile dysfunction, and in tumor invasion and metastasis (Taguchi et al., *Nature* 405: 354–357, (2000)).

In addition to AGEs, other compounds can bind to, and modulate RAGE. In normal development, RAGE interacts with amphoterin, a polypeptide which mediates neurite outgrowth in cultured embryonic neurons (Hori et al., 1995). RAGE has also been shown to interact with EN-RAGE, a protein having substantial similarity to calgranulin (Hofmann et al., Cell 97:889–901 (1999)). RAGE has also been shown to interact with β-amyloid (Yan et al., *Nature* 389: 589–595, (1997); Yan et al., *Nature* 382:685–691 (1996); Yan et al., *Proc. Natl.Acad. Sci.*, 94:5296–5301 (1997)).

Binding of ligands such as AGEs, S100/calgranulin/EN-RAGE, β-amyloid, CML (N$^\epsilon$-Carboxymethyl lysine), and amphoterin to RAGE has been shown to modify expression of a variety of genes. For example, in many cell types interaction between RAGE and its ligands generates oxidative stress, which thereby results in activation of the free radical sensitive transcription factor NF-κB, and the activation of NF-κB regulated genes, such as the cytokines IL-1β, TNF-α, and the like. In addition, several other regulatory pathways, such as those involving p21ras, MAP kinases, ERK1 and ERK2, have been shown to be activated by binding of AGEs and other ligands to RAGE. In fact, transcription of RAGE itself is regulated at least in part by NF-κB. Thus, an ascending, and often detrimental, spiral is fueled by a positive feedback loop initiated by ligand binding. Antagonizing binding of physiological ligands to RAGE, therefore, is our target for down-regulation of the pathophysiological changes brought about by excessive concentrations of AGEs and other ligands for RAGE.

Thus, there is a need for the development of compounds that antagonize binding of physiological ligands to the RAGE receptor.

SUMMARY OF THE INVENTION

This invention provides compounds which are useful as RAGE modulators. In a preferred embodiment, the present invention provides compounds of Formula (I) as depicted below, to methods of their preparation, pharmaceutical compositions comprising the compounds and to their use in treating human or animal disorders. The compounds of the invention are useful as modulators of the interaction of the receptor for advanced glycated end products (RAGE) with its ligands such as advanced glycated end products (AGEs), S100/calgranulin/EN-RAGE, β-amyloid and amphoterin, and thus are useful for the management, treatment, control, and/or as an adjunct treatment of diseases in humans caused by RAGE. Such diseases or disease states include acute and chronic inflammation, the development of diabetic late complications such as increased vascular permeability, nephropathy, atherosclerosis, and retinopathy, the development of Alzheimer's disease, erectile dysfunction, and tumor invasion and metastasis.

DETAILED DESCRIPTION OF THE INVENTION

In a first aspect, the present invention provides a compound comprising at least one moiety of the formula

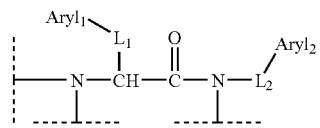

wherein $L_1$ and $L_2$ are each a hydrocarbon group of from 1 to 6 carbons or a direct bond, and Aryl$_1$ and Aryl$_2$ are aryl, wherein each of Aryl$_1$ and Aryl$_2$ are substituted by at least one lipophilic group. In a preferred embodiment, the lipophilic group is selected from C$_{1-6}$ alkyl, C$_{1-6}$ alkoxy, C$_{1-6}$ alkylaryl, or C$_{1-6}$ alkoxyaryl. We have found such compounds to be useful in the modulation, preferably in the inhibition of the interaction of RAGE with its physiological ligands, as will be discussed in more detail below.

In a second aspect, the present invention provides compounds of Formula (I):

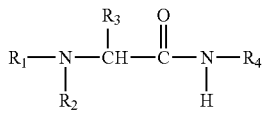
(I)

wherein
R$_1$ and R$_2$ are independently selected from
a) —H;
b) —C$_{1-6}$ alkyl;
c) -aryl;
d) —C$_{1-6}$ alkylaryl;
e) —C(O)—O—C$_{1-6}$ alkyl;
f) —C(O)—O—C$_{1-6}$ alkylaryl;
g) —C(O)—NH—C$_{1-6}$ alkyl;
h) —C(O)—NH—C$_{1-6}$ alkylaryl;
i) —SO$_2$—C$_{1-6}$ alkyl;
j) —SO$_2$—C$_{1-6}$ alkylaryl;
k) —SO$_2$-aryl;
l) —SO$_2$—NH—C$_{1-6}$ alkyl;
m) —SO$_2$—NH—C$_{1-6}$ alkylaryl;

n)
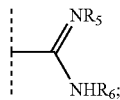

o) —C(O)—C$_{1-6}$ alkyl; and
p) —C(O)—C$_{1-6}$ alkylaryl;
R$_3$ is selected from
a) —C$_{1-6}$ alkyl;
b) -aryl; and
c) —C$_{1-6}$ alkylaryl;
R$_4$ is selected from
a) —C$_{1-6}$ alkylaryl;
b) —C$_{1-6}$ alkoxyaryl; and
c) -aryl;
R$_5$ and R$_6$ are independently selected from the group consisting of hydrogen, C$_1$–C$_6$ alkyl, C$_1$–C$_6$ alkylaryl, and aryl; and wherein the aryl and/or alkyl group(s) in R$_1$, R$_2$, R$_3$, R$_4$, R$_5$, R$_6$, R$_7$, R$_8$, R$_9$, R$_{10}$, R$_{18}$, R$_{19}$, and R$_{20}$ may be optionally substituted 1–4 times with a substituent group, wherein said substituent group(s) or the term substituted refers to groups selected from the group consisting of:
a) —H;
b) —Y—C$_{1-6}$ alkyl;
—Y-aryl;
—Y—C$_{1-6}$ alkylaryl;
—Y—C$_{1-6}$-alkyl-NR$_7$R$_8$; and
—Y—C$_{1-6}$-alkyl-W—R$_{20}$;
wherein Y and W, independently selected from the group consisting of —CH$_2$—, —O—, —N(H), —S—, SO$_2$—, —CON(H)—, —NHC(O)—,

—NHCON(H)—, —NHSO$_2$—, —SO$_2$N(H)—,
—C(O)—O—, —NHSO$_2$NH—, —O—CO—,

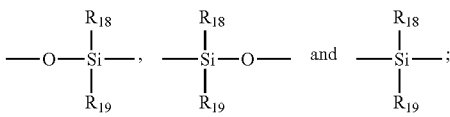

c) halogen, hydroxyl, cyano, carbamoyl, or carboxyl; and
R$_{18}$ and R$_{19}$ are independently selected from the group consisting of aryl, C$_1$–C$_6$ alkyl, C$_1$–C$_6$ alkylaryl, C$_1$–C$_6$ alkoxy, and C$_1$–C$_6$ alkoxyaryl;
R$_{20}$ is selected from the group consisting of aryl, C$_1$–C$_6$ alkyl, and C$_1$–C$_6$ alkylaryl;
R$_7$, R$_8$, R$_9$ and R$_{10}$ are independently selected from the group consisting of hydrogen, aryl, C$_1$–C$_6$ alkyl, and C$_1$–C$_6$ alkylaryl; and wherein
R$_7$ and R$_8$ may be taken together to form a ring having the formula —(CH$_2$)$_m$—X—(CH$_2$)$_n$— bonded to the nitrogen atom to which R$_7$ and R$_8$ are attached, and/or R$_5$ and R$_6$ may, independently, be taken together to form a ring having the formula —(CH$_2$)$_m$—X—(CH$_2$)$_n$— bonded to the nitrogen atoms to which R$_5$ and R$_6$ are attached, wherein m and n are, independently, 1, 2, 3, or 4; X is selected from the group consisting of —CH$_2$—, —O—, —S—, —S(O$_2$)—, —C(O)—, —CON(H)—, —NHC(O)—, —NHCON(H)—, —NHSO$_2$—, —SO$_2$N(H)—, —C(O)—O—, —O—C(O)—, —NHSO$_2$NH—,

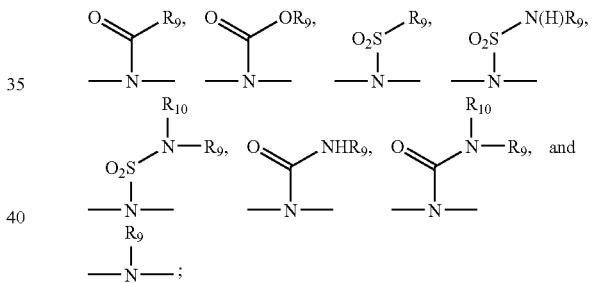

or a pharmaceutically acceptable salt, solvate or prodrug thereof.

In the compounds of Formula (I), the various functional groups represented should be understood to have a point of attachment at the functional group having the hyphen. In other words, in the case of —C$_{1-6}$ alkylaryl, it should be understood that the point of attachment is the alkyl group; an example would be benzyl. In the case of a group such as —C(O)—NH—C$_{1-6}$ alkylaryl, the point of attachment is the carbonyl carbon.

In a preferred embodiment of this aspect of the invention, the compounds of Formula (I) include those wherein:
R$_1$ is hydrogen;
R$_2$ is selected from
a) —H;
b) —C$_{1-6}$ alkyl;
c) —C$_{1-6}$ alkylaryl;
d) —C(O)—O—C$_{1-6}$ alkyl;
e) —C(O)—NH—C$_{1-6}$ alkyl;
f) —C(O)—NH—C$_{1-6}$ alkylaryl;
f) —SO$_2$—C$_{1-6}$ alkyl;
h) —SO$_2$—C$_{1-6}$ alkylaryl;
i) —SO$_2$—NH—C$_{1-6}$ alkyl; and j)

$$\begin{array}{c} NR_5 \\ | \\ -C \\ | \\ NHR_6 \end{array};$$

k) —C(O)—$C_{1-6}$ alkyl;
l) —C(O)—$C_{1-6}$ alkylaryl;
$R_3$ is selected from
  a) —$C_{1-4}$ alkylaryl; and
$R_4$ is selected from
  a) —$C_{1-6}$ alkylaryl; and
  b) -aryl;

and wherein the aryl group in $R_1$, $R_2$, $R_3$ and $R_4$ is optionally substituted 1–4 times with a substituent group, wherein said substituent group(s) or the term substituted refers to groups selected from the group consisting of:
  a) —H;
  b) —Y—$C_{1-6}$ alkyl;
    —Y-aryl;
    —Y—$C_{1-6}$ alkylaryl;
    —Y—$C_{1-6}$-alkyl-$NR_7R_8$; and
    —Y—$C_{1-6}$—W—$R_{20}$;
      wherein Y and W are, independently selected from the group consisting of —$CH_2$—, —O—, —N(H), —S—, —$SO_2$—, —CON(H)—, —NHC(O)—, —NHCON(H)—, —$NHSO_2$—, —$SO_2N(H)$—, —C(O)—O—, —$NHSO_2NH$—, —O—CO—, $$-O-\underset{R_{19}}{\overset{R_{18}}{Si}}-, \quad -\underset{R_{19}}{\overset{R_{18}}{Si}}-O- \quad \text{and} \quad -\underset{R_{19}}{\overset{R_{18}}{Si}}-;$$

c) halogen, hydroxyl, carbamoyl, and carboxyl;
$R_{18}$ and $R_{19}$ are selected from the group consisting of aryl, $C_1$–$C_6$ alkyl, $C_1$–$C_6$ alkylaryl, $C_1$–$C_6$ alkoxy, and $C_1$–$C_6$ alkoxyaryl;
$R_{20}$ is selected from the group consisting of aryl, $C_1$–$C_6$ alkyl, or $C_1$–$C_6$ alkylaryl, and wherein
$R_7$ and $R_8$ are selected from the group consisting of hydrogen, aryl, $C_1$–$C_6$ alkyl, or $C_1$–$C_6$ alkylaryl; and wherein
$R_7$ and $R_8$ may be taken together to form a ring having the formula —$(CH_2)_m$—X—$(CH_2)_n$— bonded to the nitrogen atom to which $R_7$ and $R_8$ are attached, and/or $R_5$ and $R_6$ may, independently, be taken together to form a ring having the formula —$(CH_2)_m$—X—$(CH_2)_n$— bonded to the nitrogen atoms to which $R_5$ and $R_6$ are attached, wherein m, n, and X are as defined above.

In a further preferred embodiment, the $R_3$ groups above include $C_{1-3}$ alkylaryl, said aryl optionally substituted by substituted 1–4 times with a substituent group, wherein said substituent group(s) or the term substituted refers to groups selected from the group consisting of:
    —Y—$C_{1-6}$ alkyl;
    —Y-aryl;
    —Y—$C_{1-6}$ alkylaryl;
    —Y—$C_{1-6}$-alkyl-$NR_7R_8$; and
    —Y—$C_{1-6}$-alkyl-W—$R_{20}$;
      wherein Y and W are, independently selected from the group consisting of —$CH_2$—, —O—, —N(H), —S—, —$SO_2$—, —CON(H)—, —NHC(O)—, —NH-CON(H)—, —$NHSO_2$—, —$SO_2N(H)$—, —C(O)—O—, —$NHSO_2NH$—, —O—CO—, $$-O-\underset{R_{19}}{\overset{R_{18}}{Si}}-, \quad -\underset{R_{19}}{\overset{R_{18}}{Si}}-O- \quad \text{and} \quad -\underset{R_{19}}{\overset{R_{18}}{Si}}-.$$

A further preferred embodiment is the embodiment referred to above, wherein wherein aryl is phenyl or napthyl, optionally substituted by $C_{1-6}$ alkyl, $C_{1-6}$ alkoxy, $C_{1-6}$ alkylaryl, or $C_{1-6}$ alkoxyaryl.

Also included within the scope of the invention are the individual enantiomers of the compounds represented by Formula (I) above as well as any wholly or partially racemic mixtures thereof. The present invention also covers the individual enantiomers of the compounds represented by formula above as mixtures with diastereoisomers thereof in which one or more stereocenters are inverted.

Compounds of the present invention which are preferred for their high biological activity are listed by name below in Table 1.

TABLE 1

| Example | Chemical Name |
|---|---|
| 1 | (R)-3-(2-Naphthyl)-2-aminopropionic Acid 4-Diethylaminoethoxycarbonyl-2-butoxyaniline Amide Dihydrochloride |
| 2 | (R)-3-(2-Naphthyl)-2-aminopropionic Acid 4-Methoxycarbonyl-2-butoxyaniline Amide Hydrochloride |
| 3 | (R)-3-(4-Benzyloxyphenyl)-2-tert-butoxycarbonylaminopropionic Acid 4-Diethylaminoethoxycarbonyl-2-butoxyaniline Amide |
| 4 | (R)-3-(4-Benzyloxyphenyl)-2-aminopropionic Acid 4-Diethylaminoethoxycarbonyl-2-butoxyaniline Amide Dihydrochloride |
| 5 | (R)-3-(2-Naphthyl)-2-methylaminopropionic Acid 4-Diethylaminoethoxycarbonyl-2-butoxyaniline Amide Dihydrochloride |
| 6 | (R)-3-(4-Benzyloxyphenyl)-2-tert-butoxycarbonylaminopropionic Acid 4-Methoxycarbonyl-2-hydroxyaniline Amide |
| 7 | (R)-3-(4-Benzyloxyphenyl)-2-tert-butoxycarbonylaminopropionic Acid 4-tert-Butoxycarbonyl-2-tert-butoxyaniline Amide |
| 8 | (R)-3-(4-Benzyloxyphenyl)-2-tert-butoxycarbonylaminopropionic Acid 4-Diethylaminoethoxycarbonyl-2-isobutoxyaniline Amide |
| 9 | (R)-3-(4-Benzyloxyphenyl)-2-aminopropionic Acid 4-Diethylaminoethoxycarbonyl-2-isobutoxyaniline Amide Dihydrochloride |
| 10 | (R)-3-Phenyl-2-tert-butoxycarbonylaminopropionic Acid 4-Diethylaminoethoxycarbonyl-2-butoxyaniline Amide |
| 11 | (R)-3-Phenyl-2-aminopropionic Acid 4-Diethylaminoethoxycarbonyl-2-butoxyaniline Amide Dihydrochloride |
| 12 | (R)-3-(2-Naphthyl)-2-guanidinylpropionic Acid 4-Diethylaminoethoxycarbonyl-2-butoxyaniline Amide Dihydrochloride |
| 13 | (R)-3-(4-Benzyloxyphenyl)-2-isopropylaminopropionic Acid 4-Diethylaminoethoxycarbonyl-2-butoxyaniline Amide |
| 14 | (R)-3-(4-Benzyloxyphenyl)-2-benzylaminopropionic Acid 4-Diethylaminoethoxycarbonyl-2-butoxyaniline Amide |
| 15 | (R)-3-(4-Benzyloxyphenyl)-2-methanesulfonylaminopropionic Acid 4-Diethylaminoethoxycarbonyl-2-butoxyaniline Amide |
| 16 | (R)-3-(4-Benzyloxyphenyl)-2-phenylsulfonylaminopropionic Acid 4-Diethylaminoethoxycarbonyl-2-butoxyaniline Amide |
| 17 | (R)-3-(4-Benzyloxyphenyl)-2-ethylcarbamoylaminopropionic Acid 4-Diethylaminoethoxycarbonyl-2-butoxyaniline Amide |
| 18 | (R)-3-(4-Benzyloxyphenyl)-2-tert-butylcarbamoylaminopropionic Acid 4-Diethylaminoethoxycarbonyl-2-butoxyaniline Amide |
| 19 | (R)-3-(4-Benzyloxyphenyl)-2-tert-butoxycarbonylaminopropionic Acid 4-Diethylaminoethoxy-2-diethylaminoethoxyaniline Amide |

TABLE 1-continued

| Example | Chemical Name |
|---|---|
| 20 | (R)-3-(4-Benzyloxyphenyl)-2-aminopropionic Acid 4-Diethylaminoethoxy-2-diethylaminoethoxyaniline Amide Trihydrochloride |
| 21 | (R)-3-(4-Benzyloxyphenyl)-2-tert-butoxycarbonylamino-propionic Acid 4-(3-Diethylamino-1-propoxy)-2-(3-diethyl-amino-1-propoxy)aniline Amide |
| 22 | (R)-3-(4-Benzyloxyphenyl)-2-aminopropionic Acid 4-(3-Diethylamino-1-propoxy)-2-(3-diethylamino-1-propoxyaniline Amide Trihydrochloride |
| 23 | (R)-3-(4-Benzyloxyphenyl)-2-tert-butoxycarbonylamino-propionic Acid 4-Diethylaminoethoxycarbonyl-2-(2-furyl-methoxy)aniline Amide |
| 24 | (R)-3-(4-Benzyloxyphenyl)-2-aminopropionic Acid 4-Diethylaminoethoxycarbonyl-2-(2-furylmethoxy)aniline Amide Dihydrochloride |
| 25 | (R)-3-(2-Naphthyl)-2-acetylaminopropionic Acid 4-Diethylaminoethoxycarbonyl-2-butoxyaniline Amide |
| 26 | (R)-3-(4-Benzyloxyphenyl)-2-acetylaminopropionic Acid 4-Diethylaminoethoxycarbonyl-2-butoxyaniline Amide |

Accordingly, in a further embodiment of the invention, there is provided the above compounds, or the free amine, free acid, solvate, prodrug, or pharmaceutically acceptable salt thereof.

As used herein, the term "alkyl" refers to a straight or branched chain hydrocarbon having the number of specified carbon atoms. Examples of "alkyl" as used herein include, but are not limited to, methyl, n-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkylene" as used herein include, but are not limited to, methylene, ethylene, and the like.

As used herein, the term "aryl" refers to a five- to seven-membered aromatic ring, or to an optionally substituted benzene ring system, optionally containing one or more nitrogen, oxygen, or sulfur heteroatoms, where N-oxides and sulfur monoxides and sulfur dioxides are permissible substitutions. Such a ring may be fused to one or more five- to seven-membered aromatic rings optionally containing one or more nitrogen, oxygen, or sulfur heteroatoms. Preferred aryl groups include phenyl, biphenyl, 2-naphthyl, 1-naphthyl, phenanthryl, 1-anthracenyl, pyridyl, furyl, furanyl, thiophenyl, indolyl, isothiazolyl, imidazolyl, benzimidazolyl, tetrazolyl, pyrazinyl, pyrimidyl, quinolyl, isoquinolyl, benzofuryl, isobenzofuryl, benzothienyl, benzindoyl, pyrazolyl, isoindolyl, purinyl, carbazolyl, isoxazolyl, thiazolyl, oxazolyl, benzothiazolyl, benzoxazolyl, and the like. In this regard, especially preferred aryl groups include phenyl, 2-naphthyl, 1-naphthyl, biphenyl, and like ring systems optionally substituted by tert-butyloxy, benzyloxy, n-butyloxy, ispropyloxy, and phenoxy.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the chemical structure terms "contain" or "containing" refer to in-line substitutions at any position along the above defined substituent at one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of Formula (I)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_1$–$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I): for example, the lactam formed by a carboxylic group in $R_2$ and an amine in $R_4$, and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like. The term "pharmacologically effective amount" shall mean that amount of a drug or pharmaceutical agent that will elicit the biological or medical response of a tissue, animal or human that is being sought by a researcher or clinician. This amount can be a therapeutically effective amount.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl substituents shall be recognized as being functionally equivalent to those having one or more degrees of unsaturation. Designated numbers of carbon atoms (e.g. $C_{1-6}$) shall refer independently to the number of carbon atoms in an alkyl moiety or to the alkyl portion of a larger substituent in which the term "alkyl" appears as its prefix root. Similarly, the term "$C_2$–$C_8$ alkenyl" and $C_2$–$C_8$ alkynyl" refer to groups having from 2 to 8 carbon atoms and at least one carbon-carbon double bond or carbon-carbon triple bond, respectively. The term "lower", for example in relation to "lower alkyl" refers to a $C_{1-6}$ alkyl group.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —$C(O)NH_2$.

The present invention also provides a method for the synthesis of compounds useful as intermediates in the preparation of compounds of Formula (I) along with methods for the preparation of compounds of Formula (I).

A suitably protected alpha-amino acid (1), where PG is an amine protecting group such as tert-butoxycarbonyl, is treated with an amine in the presence of a coupling reagent such as but not limited to diisopropyl carbodiimide (DIC) to form the amide (2). The α-amino group in (2) is then deprotected, employing a strong acid such as hydrogen chloride for the case where PG is tert-butoxycarbonyl, to afford the free amine (3) either as the free base or as a salt (Scheme 1). A suitably protected alpha-amino acid (1), where PG is an amine protecting group such as tert-butoxycarbonyl, is treated with an amine in the presence of a coupling reagent such as but not limited to diisopropyl carbodiimide (DIC) to form the amide (2). The α-amino group in (2) is then deprotected, employing a strong acid such as hydrogen chloride for the case where PG is tert-butoxycarbonyl, to afford the free amine (3) either as the free base or as a salt (Scheme 1).

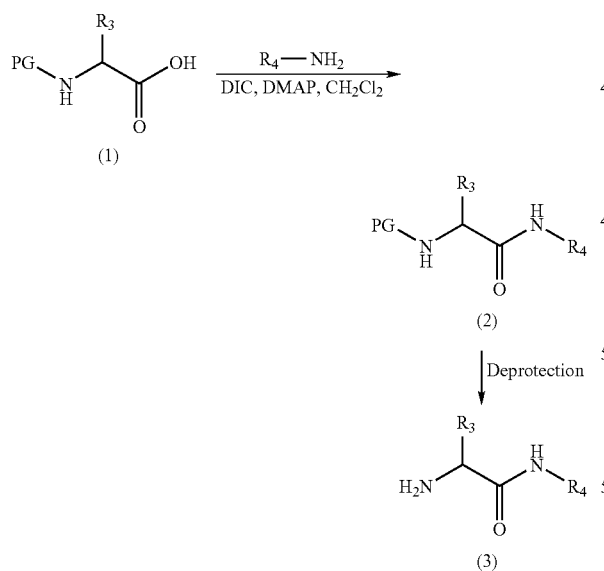

To further derivative the amino group of compound (3), the free amino compound, or the suitable salt thereof may be treated with an aldehyde or ketone $R_{12}C(O)R_{11}$ in the presence of a reducing agent such as sodium cyanoborohydride or sodium triacetoxyborohydride to afford compound (4), where $R_{12}$ and $R_{11}$ are defined such that $R_2$ in (4) conforms to the specifications for Formula (I). Alternately, the amine compound (3) may be treated with tertiary amine base such as DIEA and a molar equvalent amount (or slight excess) of an alkylating agent of general structure $R_2$-Z, where Z is is a nucleofugal group such as bromine, to form the secondary amine compound (4) (Scheme 2). Amine (3) may be treated with a tertiary amine base such as DIEA and 2 molar equivalents (or slight excess) of an alkylating agent of general structure $R_2$-Z, where Z is is a nucleofugal group such as bromine, to form the amine compound (5). Alternately, the amine compound (3) may be treated with an electron deficient olefinic compound such as but not limited to ethyl acrylate, to afford the adduct intermediate (6). Compound (6) may be manipulated, employing methods known in the art such as hydride reduction, in transforming such an adduct to compounds of general structure (4).

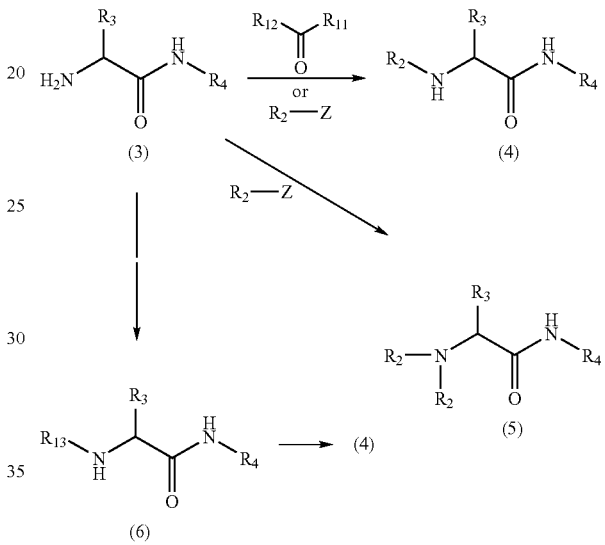

To further derivatize the amino group of compound (3), the free amino compound, or the suitable salt thereof may be treated with a sulfonyl chloride such as benzenesulfonyl chloride to form the sulfonamide (7) (Scheme 3), where $R_{14}$ is $C_{1-6}$ alkyl, $C_{1-6}$ alkylaryl, or aryl. Alternately, an amine $R_{15}$—$NH_2$ may be treated with sulfuryl chloride and the intermediate then treated with (2) to afford the sulfonylurea (7) where $R_{14}$ is —NH—$C_{1-6}$ alkyl or —NH—$C_{1-6}$ alkylaryl.

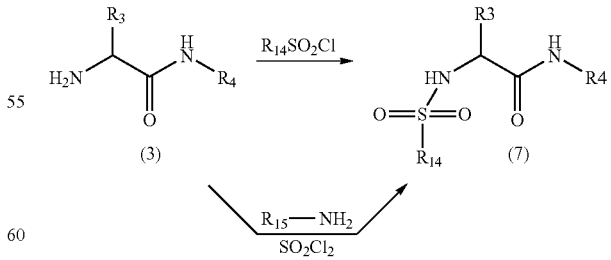

To further derivatize the amino group of compound (3), the free amino compound, or the suitable salt thereof may be treated with an isocyanate $R_{15}NCO$ in the presence or absence of a tertiary amine base such as TEA to form the urea (8) (Scheme 4), where $R_{15}$ is —$C_{1-6}$ alkyl or —$C_{1-6}$ alkylaryl and Q is NH. Alternately, compound (3) may be treated with $R_{15}O$—C(O)Cl and a tertiary amine base such as TEA to afford compound (8) where $R_{15}$ is —$C_{1-6}$ alkyl or —$C_{1-6}$ alkylaryl and Q is O.

Scheme 4

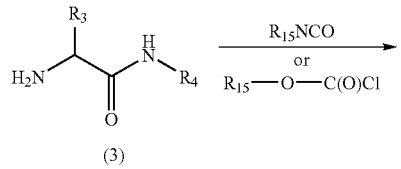

(3)

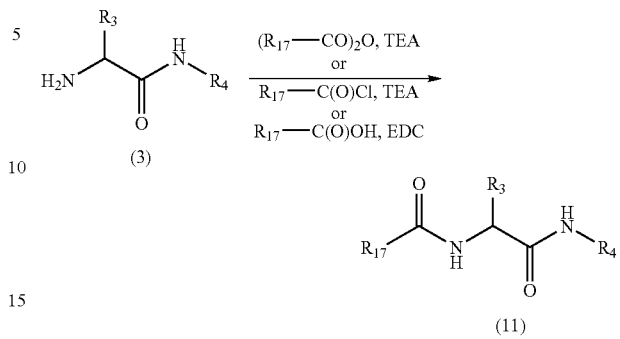

Compound (9) may be treated with triphenyl phosphine, either diisopropyl azodicarboxylate (DIAD) or diethyl azodicarboxylate (DEAD) and an alcohol $R_{16}$—OH to form the compound (10) (Scheme 5), after removal of the protecting group PG. $R_{16}$ is —$C_{1-6}$ alkyl, —$C_{1-6}$ alkylaryl, —$C_{1-6}$ alkyl-OSi($C_{1-6}$ alkyl)$_3$, —$C_{1-6}$ alkyl-OSi($C_{1-6}$ alkylaryl)$_3$, or —$C_{1-6}$ alkyl-$NR_8R_9$ (provided that neither $R_8$ nor $R_9$ are hydrogen). PG may be, for example, tert-butoxycarbonyl, benzyloxycarbonyl, and the like.

Scheme 5

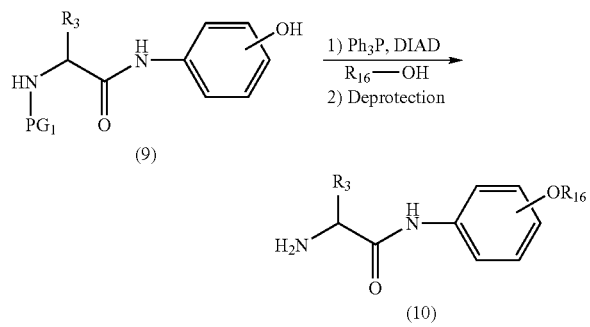

Compound (3) or a suitable salt thereof may be treated with a acid anhydride ($R_{17}$—CO)$_2$O and a base such as TEA in the presence or absence of pyridine or DMAP to afford compound (11) (Scheme 6). The substituent $R_{17}$ may be chosen such that the group $R_{17}$—C(O)— is as specified for $R_2$ in Formula (I). Alternately, compound (3) may be treated with the acid chloride $R_{17}$—COCl and an tertiary amine base such as TEA in the presence or absence of pyridine or DMAP to afford compound (11). Alternately, compound (3) may be treated with the carboxylic acid $R_{17}$—$CO_2H$ and a carbodiimide reagent (i.e., a "coupling reagent") such as EDC, DIC, or DCC in the presence or absence of HOBt to provide compound (11).

Scheme 6

Compound (3) or a suitable salt thereof may be treated (Scheme 7) with an activated amidine reagent such as N,N'-bis-BOC-1-guanylpyrazole or 3,5-dimethylpyrazole-1-carboxamidine nitrate in the presence of a tertiary organic base such as TEA to generate the guanidine compound. Guanidine substituent protecting groups may be removed. For example, where N,N'-bis-BOC-1-guanylpyrazole is employed, the BOC groups of the adduct may be removed with a strong acid such as hydrogen chloride to afford the free guanidine compound (12), where $R_5$ and $R_6$ are as defined for Formula (I).

Scheme 7

GENERAL EXPERIMENTAL

LC-MS data was obtained using gradient elution on a Waters 600 controller equipped with a 2487 dual wavelength detector and a Leap Technologies HTS PAL Autosampler using an YMC Combiscreen ODS-A 50×4.6 mm column. A three minute gradient was run from 25% B (97.5% acetonitrile, 2.5% water, 0.05% TFA) and 75% A (97.5% water, 2.5% acetonitrile, 0.05% TFA) to 100% B. The MS was a Micromass ZMD instrument. All data was obtained in the positive mode unless otherwise noted. $^1$H NMR data was obtained on a Varian 300 MHz spectrometer.

Abbreviations used in the Examples are as follows:
APCI=atmospheric pressure chemical ionization
BOC=tert-butoxycarbonyl
BOP=(1-benzotriazolyloxy)tris(dimethylamino)phosphonium hexafluorophosphate
d=day
DIAD=diisopropyl azodicarboxylate
DCC=dicyclohexylcarbodiimide DCM=dichloromethane
DIEA=diisopropylethylamine
DMF=N,N-dimethylformamide
DMPU=1,3-dimethypropylene urea
DMSO=dimethylsulfoxide
EDC=1-ethyl-3-(3-dimethylaminopropyl)-carbodiimide hydrochloride
EDTA=ethylenediamine tetraacetic acid
ELISA=enzyme-linked immunosorbent assay
ESI=electrospray ionization
ether=diethyl ether
EtOAc=ethyl acetate
FBS=fetal bovine serum
g=gram
h=hour
HBTU=O-benzotriazol-1-yl-N,N,N',N'-tetramethyluronium hexafluorophosphate
HMPA=hexamethylphosphoric triamide
HOBt=1-hydroxybenzotriazole
Hz=hertz
i.v.=intravenous
kD=kiloDalton
L=liter
LAH=lithium aluminum hydride
LDA=lithium diisopropylamide
LPS=lipopolysaccharide
M=molar
m/z=mass to charge ratio
mbar=millibar
MeOH=methanol
mg=milligram
min=minute
mL=milliliter
mM=millimolar
mmol=millimole
mol=mole
mp=melting point
MS=mass spectrometry
N=normal
NMM=N-methylmorpholine, 4-methylmorpholine
NMR=nuclear magnetic resonance spectroscopy
p.o.=per oral
PBS=phosphate buffered saline solution
PMA=phorbol myristate acetate
ppm=parts per million
psi=pounds per square inch
$R_f$=relative TLC mobility
rt=room temperature
s.c.=subcutaneous
SPA=scintillation proximity assay
TEA=triethylamine
TFA=trifluoroacetic acid
THF=tetrahydrofuran
THP=tetrahydropyranyl
TLC=thin layer chromatography
$T_r$=retention time The following compounds are synthesized according to the Schemes.

Example 1

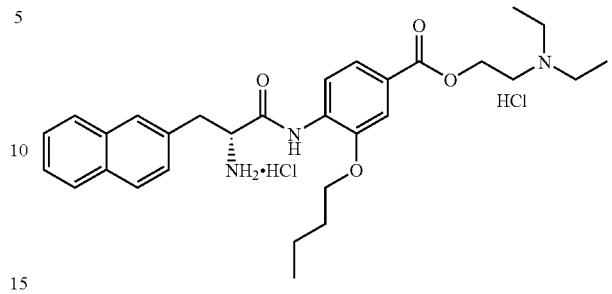

To a solution of BOC-2-naphthyl-(D)-alanine (3.15 g) in $CH_2Cl_2$ (40 mL), HOBt (1.35 g) and DCC (2.2 g) were added at rt under nitrogen atmosphere. After 2 h $NEt_3$ (2.79 mL) and 4-diethylaminoethoxycarbonyl-2-butoxyaniline hydrochloride (3.8 g) were added followed by DMAP (122 mg). The reaction mixture is then stirred at rt for 3 d and filtered to remove dicyclohexylurea. The filtrate is concentrated and purified by silica gel column chromatography to afford 4.8 g of the amide Intermediate 1A. $^1H$ NMR (CDCl3): 8.50 (d, 1H), 8.27 (br s, 1H), 7.55–7.85 (m, 5H), 7.25–7.45 (m, 5H), 5.15 (br s, 1H), 4.60 (br s, 1H), 4.38 (t, 2H), 3.6–3.9 (m, 2H), 3.30 (d, 2H), 2.82 (t, 2H), 2.60 (q, 4H), 1.2–1.8 (m, 10H), 1.10 (t, 6H).

MS: m/z 606 $(M+H)^+$ 120 mg of Intermediate 1A obtained above is stirred in 4 M HCl in dioxane (2 mL) for 3 h. Solvent is then removed in vacuo and the residue obtained is treated with ether and stirred. The ether is decanted off and the ether wash is repeated twice more. The product is then dried under vacuum to afford a pale yellow solid (90 mg), Example 1.

LC: $T_r$ 1.53; MS: 506 $(M+H)^+$

Example 2

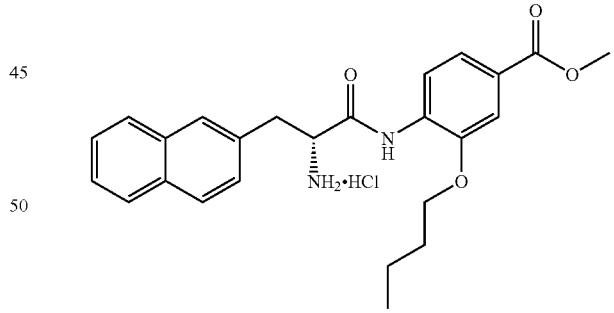

Example 1 (115 mg) is dissolved in anhydrous methanol (5 mL) and treated with 1M KOH in methanol (25 μL). The reaction mixture is stirred overnight at rt and added with 2 drops of acetic acid and stirred. Solvent is then removed in vacuo and the residue obtained is purified by silica gel column chromatography to yield the methyl ester Intermediate 2A (65 mg).

NMR (acetone-d6): 9.10 (br s, 1H), 8.42 (d, 2H), 7.20–7.80 (m, 7H), 6.78 (br d, 1h), 4.50 (br m, 1H), 4.0 (br m, 2H), 3.76 (s, 3H), 3.20 (dd, 1H), 2.9–3.2 (m, 4H), 1.22 (q, 2H), 1.20 (s, 9H), 0.90 (t, 3H).

MS: m/z 521 $(M+H)^+$

Intermediate 2A is dissolved in 4M HCl in dioxane (2 mL) and stirred at rt for 3 h. Product is isolated as for Example 1 to afford Example 2 as a fluffy white solid (50 mg).
MS: m/z 421 (M+H)+

Example 3

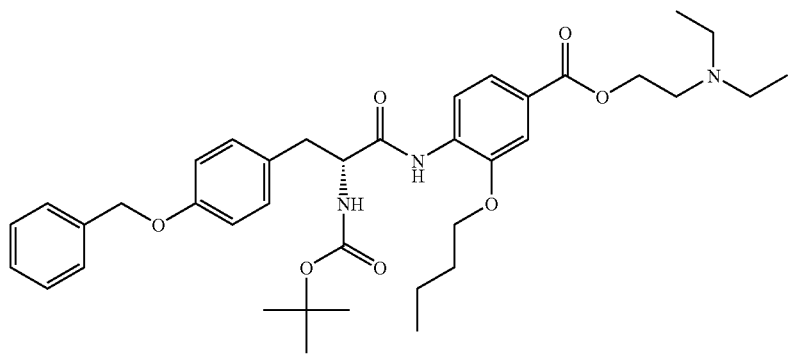

To a solution of BOC-D-Tyr(Bzl)-OH (1.11 g) in CH$_2$Cl$_2$ (15 mL), HOBT (406 mg) and DCC (681 mg) were added at rt. After 2 h TEA (840 μL) and 4-diethylaminoethoxycarbonyl-2-butoxyaniline hydrochloride (1.04 g) were added followed by DMAP (36 mg). The reaction mixture is then stirred at rt for 3 d and filtered to remove dicyclohexylurea. The filtrate is concentrated and purified on a silica gel column chromatography to afford 1.2 g of Example 3.
LC: T$_r$ 2.18; MS: m/z 662 (M+H)+

Example 4

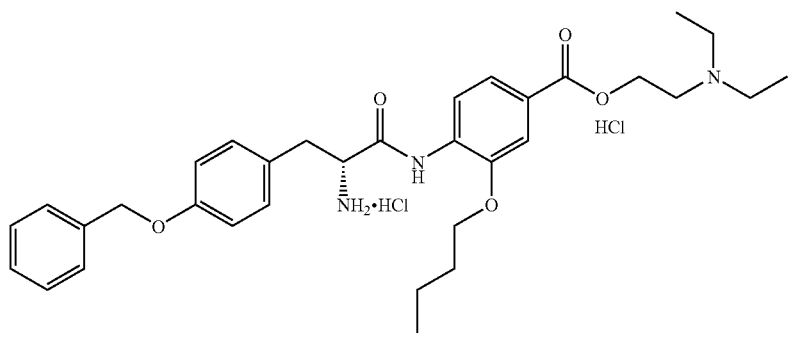

165 mg of Example 3 is stirred in 4M HCl in dioxane (2 mL) for 3 h. Product is isolated as for Example 1 to afford Example 4 as a pale yellow solid (105 mg).
LC: T$_r$ 1.75; MS: m/z 562(M+H)+

Example 5

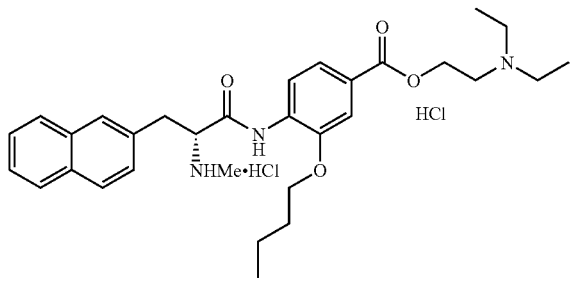

BOC-(2-naphthyl)-D-alanine (946 mg) is dissolved in anhydrous THF at rt, added with methyl iodide (1.5 mL) and cooled to 0° C. Solid NaH (400 mg; 60% dispersion in oil) is slowly added to it and the reaction is allowed to proceed overnight with gradual warming up to rt. After 24 h the reaction mixture is diluted with a mixture of EtOAc and cold water and stirred. The contents were then shaken a separatory funnel and the layers were separated. The aqueous layer is then extracted with EtOAc. The organic extracts were combined, ished with water and brine and dried over anhydrous sodium sulfate. Solvent is removed in vacuo and the residue obtained is purified by silica gel column chromatography to afford the acid Intermediate 5A (630 mg).

MS: m/z 230 (M+H)$^+$

To a solution of Intermediate 5A obtained as above (616 mg) in CH$_2$Cl$_2$ (10 mL), HOBt (303 mg) and DCC (463 mg) were added at rt under nitrogen atmosphere. After 2 h triethylamine (651 μL) and 4-diethylaminoethoxycarbonyl-2-butoxyaniline hydrochloride (645 mg) were added followed by DMAP (36 mg). The reaction mixture is then stirred at rt for 4 d and filtered to remove dicyclohexylurea. The filtrate is concentrated and purified on a silica gel column chromatography to afford Intermediate 5B (220 mg).

LC: T$_r$ 2.45 min; MS: m/z 620 (M+H)$^+$

Intermediate 5B is then dissolved in 4M HCl in dioxane (4 mL) for 3 h. Product is isolated as for Example I to afford Example 5 (160 mg).

MS: m/z 520 (M+H)$^+$

Example 6

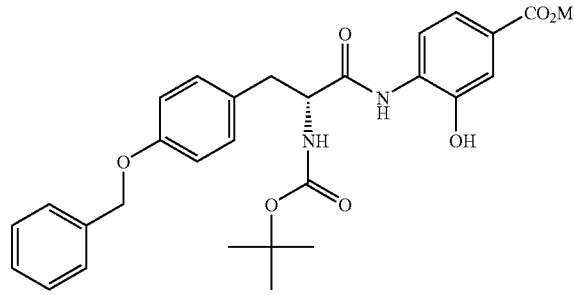

BOC-D-Tyr(Bzl)-OH (4.46 g, 12.0 mmol) is suspended in 50 mL of DCM and to this is added DCC (2.72 g, 13.20 mmol) and HOBt (1.62 g, 12.01 mmol) and the mixture stirred under nitrogen for 2 h. Triethylamine (3.3 mL) is added followed by 4-amino-3-hydroxy benzoic acid methyl ester (2.67 g, 13.20 mmol). The mixture is stirred for 4 d. The reaction mixture is filtered and the solid residue washed with DCM. The filtrate is then washed with 5% Na$_2$CO$_3$ solution (2×50 mL) followed by brine solution. The organic extract is dried over Na$_2$SO$_4$, filtered and concentrated and purified by flash chromatography on silica gel eluted with EtOAc/hexanes (50:50) to obtain Example 6 as a solid (5.0 g).

MS: m/z 521 (M+H)$^+$

Example 7

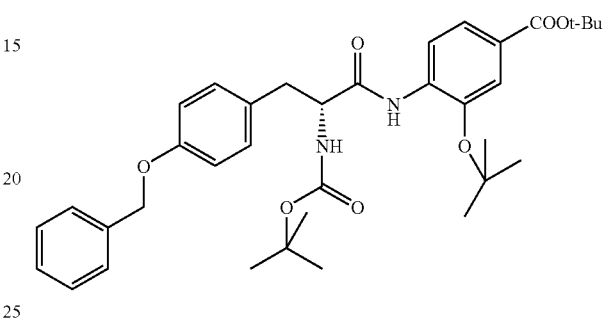

The compound of Example 6 is saponified to afford the carboxylic acid by the general method employed in preparation of Intermediate 2A, to afford Intermediate 7A.

Intermediate 7A (0.050 g, 0.099 mM) in 3 mL of DCM is added 2 drops each of BF$_3$Et$_2$O and H$_3$PO$_4$. The solution is then transferred to −78° C. and isobutylene gas bubbled through for 3 min and then allowed to warm to rt and stirred for 12 h. The solution is extracted with saturated NaHCO$_3$ (2×10 mL), dried over Na$_2$SO$_4$ and concentrated to an oil which is purified on silica gel eluted with EtOAc/hexanes (30:70) to obtain Example 7 as a white solid (0.055 g).

MS: m/z 619 (M+H)$^+$

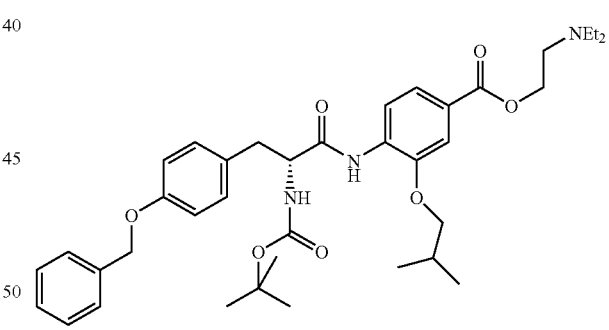

To Example 6 (0.05 g, 0.096 mmol) in 1 mL of TBF is added 6 uL of isobutyl alcohol and triphenylphosphine (0.025 g, 0.096 mmol) followed by dropwise addition of diisopropyl azodicarboxylate (0.019 g, 0.096 mmol) at 0° C. The reaction is allowed to warm to rt and stirred for 18 h. The solvent is removed under reduced pressure and the oil obtained purified by flash chromatography on silica gel eluting with EtOAc/hexane (30:70) to yield Intermediate 8A as an oil (43.6 mg, 79%). Intermediate 8A is hydrolyzed to with 1M KOH solution in dioxane at 80° C. to provide the acid Intermediate 8B (0.015 g).

Intermediate 8B (0.015 g, 0.026 mmol) is dissolved in 1 mL of DCM and HBTU (0.020 g, 0.054 mmol) added. The mixture is stirred for 1 h and 100 uL of TEA is added followed by N,N-diethylethanolamine (0.021 g, 0.180 mmol). The resulting solution is stirred for 18 h. After concentrating under reduced pressure, the crude product is purified on silica gel eluted with EtOAc/hexane (50/50) to provide Example 8 as a solid (0.014 g).

LC: T$_r$ 2.20 min; MS:m/z 662 (M+H)$^+$

Example 9

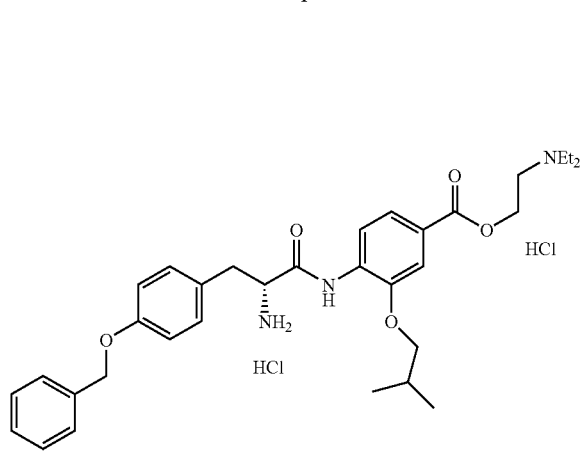

Example 8 (7 mg) is treated with 4N HCl/dioxane as described or Intermediate 1A. The product (5 mg) is isolated as for Example 1 to afford Example 9.

MS: m/z 552 (M+H)$^+$

Example 10

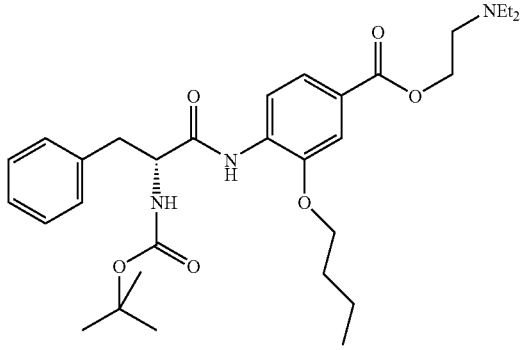

To a solution of BOC-D-phenylalanine (1.33 g) in DCM (15 mL), HOBT (743 mg) and DCC (1.24 g) were added at rt. After 2 h TEA (1.2 mL) and 4-diethylaminoethoxycarbonyl-2-butoxyaniline hydrochloride (1.73 g) were added followed by DMAP (60 mg). The reaction mixture is then stirred at rt for 3 d and filtered to remove dicyclohexylurea. The filtrate is concentrated and purified on a silica gel column chromatography to afford 1.9 g of Example 10.

LC: T$_r$ 2.05 min; MS: m/z 556 (M+H)$^+$

Example 11

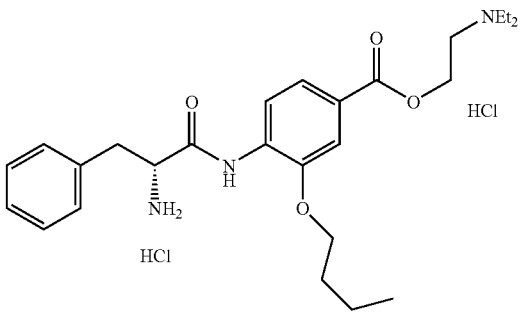

Example 10 (47 mg) is stirred in 4M HCl in dioxane (2 mL) for 3 h. Product is isolated as for Example 1 to afford Example 11 as a pale yellow solid (38 mg).

C: T$_r$ 0.83 min; MS: m/z 456 (M+H)$^+$

Example 12

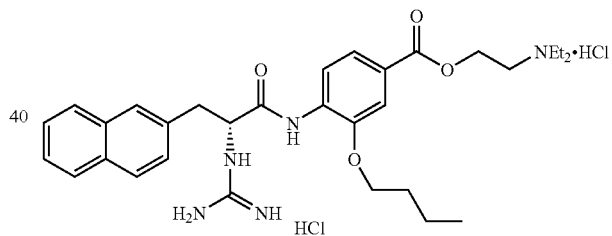

Example 1 (80 mg) is dissolved in anhydrous acetonitrile (3 mL) and treated with DIEA (60 μL) and N,N'-bis-BOC-1-guanylpyrazole (60 mg). The resulting mixture is then refluxed overnight. The reaction mixture is then cooled to rt and diluted with EtOAc (5 mL). The mixture is washed with water and brine and dried over anhydrous sodium sulfate. Solvent is removed in vacuo and the residue obtained is purified by silica gel column chromatography to afford the BOC-protected guanadino product Intermediate 12A (12 mg).

NMR: (acetone-d6) 8.8 (br s, 1H), 8.20 (d, 1H), 7.2–7.8 (m, 9H), 4.95 (dd, 1H), 4.2 (br s, 2H), 3.65–3.85 (m, 4H), 3.0–3.3 (m, 4H), 1.25 (s, 9H), 1.20 (m, 4H), 1.15 (s, 9H), 0.95 (3, 3H)

MS: m/z 748 (M+H)$^+$

Intermediate 12A (12 mg) is treated with 4M HCl/dioxane (0.5 mL) to remove the BOC group as described for Intermediate 1A, affording Example 12 (4 mg).

MS: m/z 549 (M+H)$^+$

Example 13

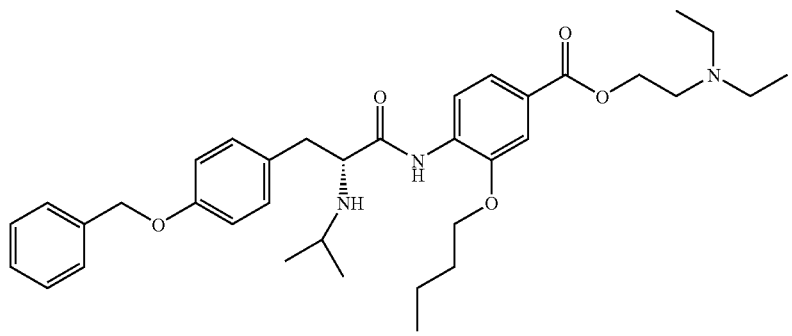

53 mg (0.084 mmole) of Example 4 is dissolved in 5 mL methanol. To this is added 10 µL of acetone. After 40 min, 0.10 mL of 1 M sodium cyanoborohydride in THF is added. The reaction is stirred overnight, the solvent removed in vacuo, and the crude compound purified by flash chromatography on silica gel (4:1 hexane: EtOAc, 10% TEA) to yield 22 mg of Example 14.

LC: $T_r$ 1.77 min; MS: m/z 603 (M+H)$^+$ 106 mg (0.168 mmol) of Example 4 is dissolved in 5 mL methanol. To this is added 60 µL of benzaldehyde, with stirring. After 12 h, 0.50 mL of 1 M sodium cyanoborohydride in THF is added. The reaction is stirred overnight, the solvent removed in vacuo, and the crude compound purified by flash chromatography on silica gel (4:1 hexane: EtOAc, 10% TEA) to yield 48.3 mg of Example 14.

LC: $T_r$ 1.83 min; MS: m/z 653 (M+H)$^+$

Example 14

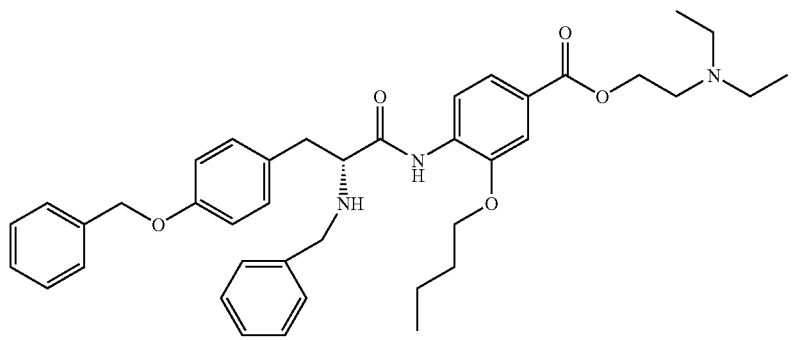

Example 15

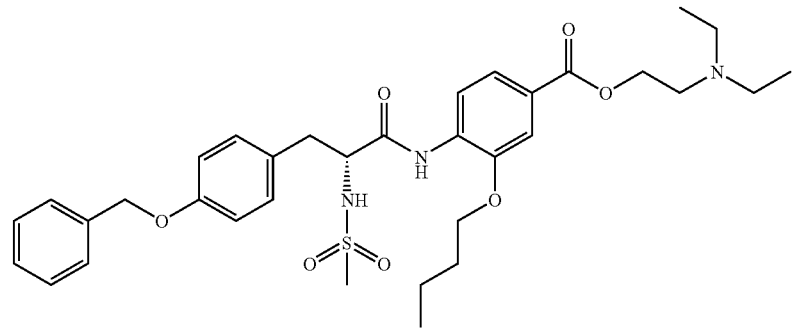

12 mg (0.019 mmole) of Example 4 is suspended in 3.5 mL dry DCM. To this is added 10 μL of methanesulfonyl chloride (0.13 mmole). The reaction is stirred overnight, then an additional 10 μL of methanesulfonyl chloride is added and the reaction allowed to stir for an additional 24 h. The solvent is removed in vacuo to yield 12.2 mg of Example 15.

LC: $T_r$ 1.99 min; MS: m/z 640 (M+H)$^+$

Example 16

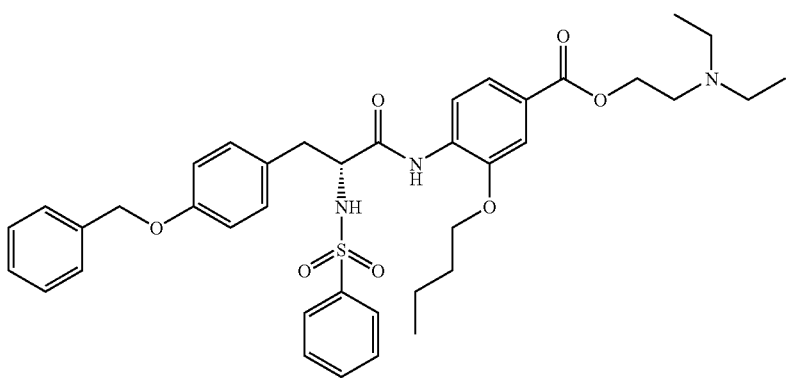

15 mg (0.024 mmole) of Example 4 is suspended in 4.0 mL dry DCM. To this is added 10 μL (0.078 mmole) of benzenesulfonyl chloride. The reaction is stirred overnight, then an additional 10 μL of benzenesulfonyl chloride is added and the reaction allowed to stir for an additional 24 h. The solvent is removed in vacuo to yield 16.8 mg of Example 16.

LC: $T_r$ 2.05 min; MS: m/z 702 (M+H)$^+$

Example 17

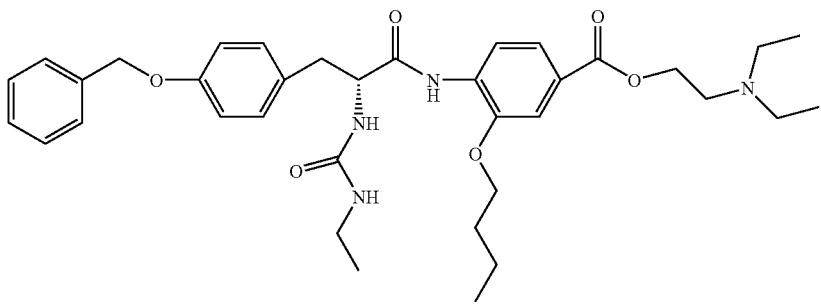

25 mg (0.040 mmole) of Example 4 is suspended in 5 mL dry DCM. To this is added 50 μL of ethyl isocyanate (0.63 mmole). The reaction is stirred overnight, and the solvent is removed in vacuo to yield 25.2 mg of Example 17.

LC: $T_r$ 1.99 min; MS: m/z 633 (M+H)$^+$

Example 18

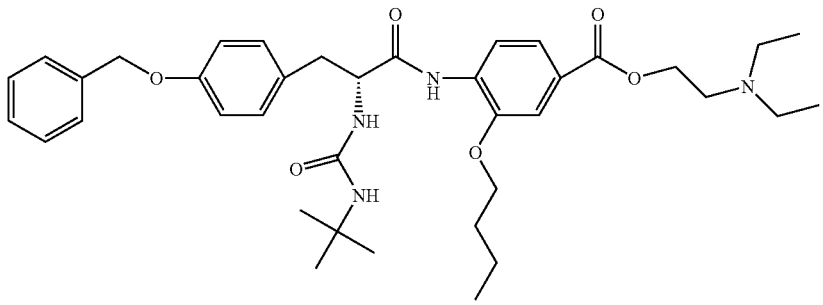

20 mg (0.032 mmole) of Example 4 is suspended in 5 mL dry DCM. To this is added 50 μL of tert-butyl isocyanate (0.44 mmole, 13.7 eq.). The reaction is stirred overnight, then an additional 50 μL of tert-butyl isocyanate is added and the reaction allowed to stir for an additional 24 h. The solvent is removed in vacuo to yield 21.1 mg of Example 18.

LC: $T_r$ 1.97 min; MS: m/z 661 (M+H)$^+$

Example 19

To a solution of BOC-D-Tyr(Bzl)-OH (279 mg) and 4-aminoresorcinol hydrochloride (135 mg) in acetonitrile (2 mL) at rt, HBTU (285 mg) and pyridine (145 μL) were added in succession. The resulting mixture is stirred overnight. The deep reddish reaction mixture is diluted with EtOAc/water (5 mL/3 mL) and the layers were separated. The aqueous layer is further extracted with EtOAC (5 mL). The organic layers were combined and washed with water and brine and dried over Na$_2$SO$_4$. The solution is filtered and the solvent is removed in vacuo. The resulting crude product is purified by silica gel column chromatography using methanol/CHCl$_3$/hexane (1:20:20) as eluent to afford 300 mg of the amide Intermediate 19A.

LC:$T_r$ 2.17 min; MS:m/z 479 (M+H)$^+$ 120 mg of Intermediate 19A is dissolved in THF (2 mL) at rt and added with triphenyl phosphine (197 mg), and N,N-diethylaminoethanol (100 μL). The resulting solution is cooled to 0° C. and treated with diisopropyl azodicarboxylate (DIAD) (152 mg). The reaction is allowed to proceed overnight with gradual warming up to rt. The reaction mixture is diluted with EtOAc/water (5 mL/3 mL) and the layers were separated. The aqueous layer is further extracted with EtOAc (5 mL). The organic layers were combined and washed with water and brine and dried over Na$_2$SO$_4$. The solution is filtered and the solvent is removed in vacuo. The resulting crude product is purified by silica gel column chromatography using NEt$_3$/methanol/CHCl$_3$/hexane (1:2:40:40) as eluent to afford 100 mg of Example 19.

LC: $T_r$ 1.80 min; MS: m/z 677 (M+H)$^+$

Example 20

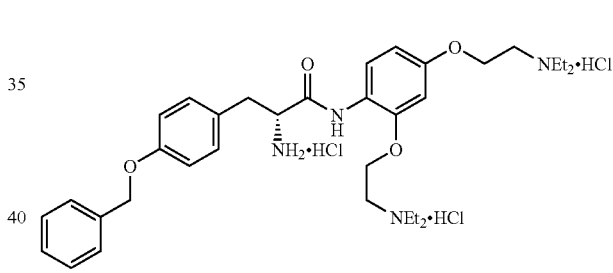

50 mg of Example 19 is stirred in 4M HCl in dioxane (1 mL) for 3 h. Product is isolated as for Example 1 to afford Example 21 as a pale yellow solid (35 mg).

MS: m/z 576 (M+H)$^+$

Example 21

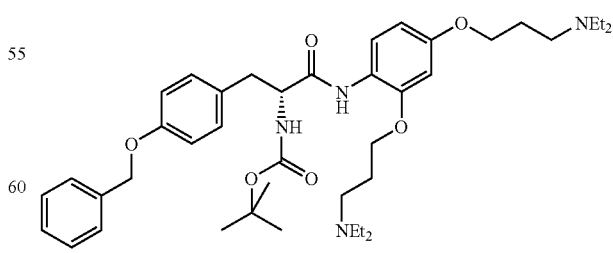

120 mg of Example 19 is dissolved in THF (2 mL) at rt and added with triphenyl phosphine (197 mg), and N,N-diethylaminopropanol (115 μL). The resulting solution is cooled to 0° C. and added with diisopropyl azodicarboxylate (DIAD) (152 mg). The reaction is allowed to proceed overnight with gradual warming up to rt. The reaction mixture is diluted with EtOAc/water (5 mL/3 mL) and the layers were separated. The aqueous layer is further extracted with EtOAc (5 mL). The organic layers were combined and washed with water and brine and dried over Na$_2$SO$_4$. The solution is filtered and the solvent is removed in vacuo. The resulting crude product is purified by silica gel column chromatography using triethylamine/methanol/CHCl$_3$/hexane (1:2:40:40) as eluent to afford 50 mg of Example 21.

LC: T$_r$ 1.84 min; MS: m/z 705 (M+H)$^+$

Example 22

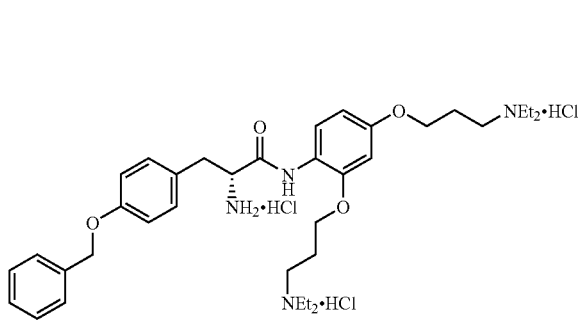

30 mg of Example 21 is stirred in 4M HCl in dioxane (1 mL) for 3 h. Product is isolated as for Example 1 to afford Example 22 as a pale yellow solid (20 mg).

MS: m/z 604 (M+H)$^+$

Example 23

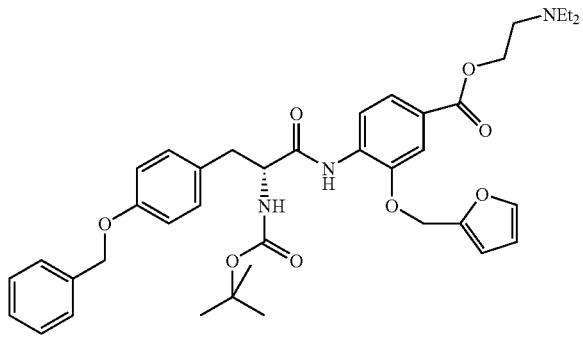

To example 6 (0.05 g, 0.096 mmol) in 1 mL of THF is added 6 uL of furfuryl alcohol and triphenylphosphine (0.025 g, 0.096 mmol) followed by dropwise addition of diisopropyl azodicarboxylate (0.019 g, 0.096 mmol) at 0° C. The reaction is allowed to warm to rt and stirred for 18 h. The solvent is removed under reduced pressure and the oil obtained purified by flash chromatography on silica gel eluting with EtOAc/hexane (30:70) to yield the aryl ether Intermediate 23A as an oil (43.0 mg). Intermediate 23A is hydrolyzed to the carboxylic acid using 1M KOH solution in dioxane at 80° C. The acid obtained (0.02 g, 0.036 mmol) is dissolved in 1 mL of DCM and HBTU (0.015 g, 0.039 mmol) added. The mixture is stirred for 1 h and 36 uL of TEA is added followed by N,N-diethylethanolamine (0.015 g, 0.130 mmol). The resulting solution is stirred for 18 h. After concentrating under reduced pressure, the crude product is purified on silica gel eluting with EtOAc/hexane (1:1) to obtain Example 23 as a solid (0.015 g).

MS: m/z 686 (M+H)$^+$

Example 24

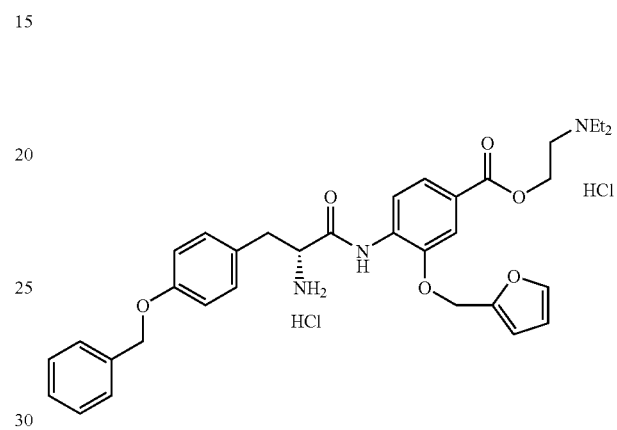

Example 23 (7 mg) is treated with 4N HCl/dioxane as described for Intermediate 1A, and the product is isolated as for Example 1 to obtain Example 24 (4 mg).

LC: T$_r$ 1.87 min; MS: m/z 586 (M+H)$^+$

Example 25

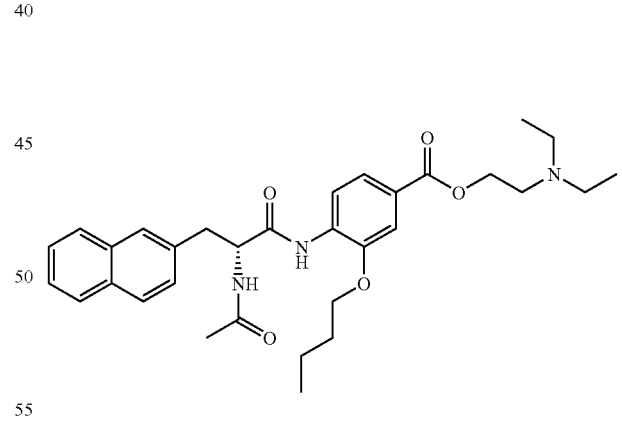

20 mg of Example 1 is dissolved in pyridine (100 μL) and treated with acetic anhydride (100 μL) at rt and stirred for 1 h. The reaction mixture is added with ice/water mixture and extracted with EtOAc. The organic layers were combined and washed with 5% aqueous CuSO$_4$, water and brine and dried over Na$_2$SO$_4$. The solution is filtered and the solvent is removed in vacuo to provide Example 25 as a pale white solid (15 mg).

LC: T$_r$ 1.90 min; MS:m/z 548 (M+H)$^+$

Example 26

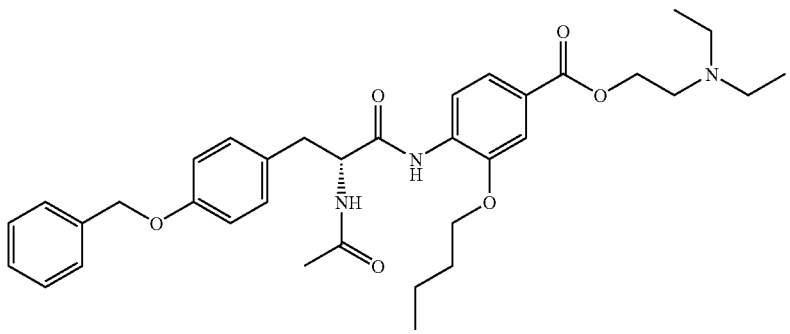

30 mg of Example 4 is dissolved in pyridine (200 μL) and treated with acetic anhydride (150 μL) at rt and stirred for 1 h. The reaction mixture is treated with ice/water mixture and extracted with EtOAC. The organic layers were combined and washed with 5% aqueous $CuSO_4$, water and brine and dried over $Na_2SO_4$. The solvent is removed in vacuo to provide Example 26 as a pale white solid (25 mg).

LC: $T_r$ 1.97 min; MS: m/z 604 $(M+H)^+$

In the above schemes, "PG" represents an amino protecting group. The term "amino protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2(methylsulfonyl)ethoxycarbonyl, 2-(triphenylphosphino)ethoxycarbonyl, 9-fluorenylmethoxycarbonyl ("FMOC"), t-butoxycarbonyl ("BOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Preferred amino-protecting groups are the allyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. Further examples of groups referred to by the above terms are described by J. W. Barton, "Protective Groups In Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino-protecting group discussed above.

In Scheme 1, other methods of coupling or acylating the protected amino acid to the compound of formula $R^4NH_2$ can be utilized, for example DCC/HBT, HBTU, and BOP and other methods, including but not limited to those listed in: Fernando Albericio and Louis A. Carpino "Coupling Reagents and Activation" in Methods in Enzymology vol.289 (Gregg B. Fields ed), pp 104–126, Academic Press, San Diego, 1997.

I. Biological Assay

The following assay method is utilized to identify compounds of Formula (I) which are effective in binding with RAGE, and hence useful as modulators, preferably antagonists of RAGE. This method is also described in U.S. Pat. No. 6,908,741.

General Assay Procedure

S100, β-amyloid and CML (500 ng/100 μL/well) in 100 mM sodium bicarbonate/sodium carbonate buffer (pH 9.8) is loaded onto the wells of a NUNC Maxisorp flat bottom 96-well microtitre plate. The plate is incubated at 4° C. overnight. The wells are aspirated and treated with 50 mM imidazole buffer saline (pH 7.2) (with 1 mM $CaCl_2/MgCl_2$) containing 1% bovine serum albumin (BSA) (300 μL/well) for two h at 37° C. The wells are aspirated and washed 3 times (400 μL/well) with 155 mM NaCl pH 7.2 buffer saline and soaked 10 seconds between each wash.

Test compounds are dissolved in nanopure water (concentration: 10–100 μM). DMSO may be used as co-solvent.

25 μL of test compound solution in 2% DMSO is added, along with 75 μL sRAGE ($4.0 \times 10^{-4}$ mg/mL FAC) to each well and samples are incubated for 1 h at 37° C. The wells are washed 3 times with 155 mM NaCl pH 7.2 buffer saline and are soaked 10 seconds between each wash. Non-radioactive binding is performed by adding:

10 μL Biotinylated goat F(ab')2 Anti-mouse IgG. ($8.0 \times 10^{-4}$ mg/mL, FAC)

10 μL Alk-phos-Sterptavidin ($3 \times 10^{-3}$ mg/mL FAC)

10 μL Polyclonal antibody for sRAGE (FAC $6.0 \times 10^{-3}$ mg/mL) to 5 mL 50 mM imidazole buffer saline (pH 7.2) containing 0.2% bovine serum albumin and 1mM $CaCl_2$. The mixture is incubated for 30 minutes at 37° C. 100 μL complex is added to each well and incubation is allowed to proceed at rt for 1 h. Wells are washed 3 times with wash buffer and soaked 10 s between each wash. 100 μL 1 mg/mL (PNPP) in 1 M diethanolamine (pH adjusted to 9.8 with HCl) is added. Color is allowed to develop in the dark for 1 to 2 h at rt. The reaction is quenched with 10 μL of stop solution (0.5 N NaOH in 50% ethanol) and the absorbance is measured spectrophotometrically with a microplate reader at 405 nm.

The following compounds of Formula 1 were synthesized according to the Schemes and tested according to the assay method described above.

$IC_{50}$ (μM) of ELISA assay represents the concentration of compound at which 50% signal has been inhibited.

Compound inhibition of S-100b/RAGE interaction in Glioma cells by Example 1 had an IC50 of 3.3 μM. Thus, the cell based assay demonstrated effective correlation with the binding of ELISA $IC_{50}$ value (1.75 μM).

| Functional Assay $IC_{50}$ (μM) | | |
|---|---|---|
| Example No. | Inhibition of NF-κB in Glioma Cells | ELISA Assay (S-100b) |
| 1 | 3.3 | 1.75 |

| ELISA Assay $IC_{50}$ (μM) | | | |
|---|---|---|---|
| Example No. | S-100b | Amyloid-β | Carboxymethyl Lysine (CML) |
| 1 | 1.75 | 3.4 | 2.29 |
| 2 | 5.1 | — | 3.16 |
| 3 | 1.32 | 1.5 | 1.5 |
| 4 | 0.82 | 2.2 | 1.12 |
| 5 | 2.88 | 1.81 | 1.27 |
| 6 | 6.3 | NA | NA |
| 7 | 1–3 | — | 8 |
| 8 | 2.0 | NA | NA |
| 9 | 1.6 | NA | NA |
| 10 | 0.95 | NA | NA |
| 11 | 10–30 | NA | NA |
| 12 | 0.3–1.0 | 5 | 0.7 |
| 13 | 1 | 1 | 0.7 |
| 14 | 2.8 | NA | NA |
| 15 | 10–30 | NA | NA |
| 16 | 20–30 | NA | NA |
| 17 | 10 | NA | NA |
| 18 | 2.3 | 2 | 0.84 |
| 19 | 1.14 | 0.80 | 0.80 |
| 20 | 0.84 | 1 | 1 |
| 21 | 0.64 | 1.23 | 0.46 |
| 22 | 0.92 | 1.73 | 0.68 |
| 23 | 15.5 | NA | NA |
| 24 | 2.7 | NA | NA |
| 25 | 15 | NA | NA |
| 26 | 5.6 | NA | NA |

NA = ELISA assay data not available

The invention further provides pharmaceutical compositions comprising the RAGE modulating compounds of the invention. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles. The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines. Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1–19.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug therof, and one or more pharmaceutically acceptable carriers, excipients, or diluents.

The compounds of the present invention selectively act as modulators of RAGE binding to a single endogenous ligand, i.e., selective modulators of β-amyloid-RAGE interaction, and therefore are especially advantageous in treatment of Alzheimer's disease and related dementias.

Further, the compounds of the present invention act as modulators of RAGE interaction with two or more endogenous ligands in preference to others. Such compounds are advantageous in treatment of related or unrelated pathologies mediated by RAGE, i.e., Alzheimer's disease and cancer.

Further, the compounds of the present invention act as modulators of RAGE binding to each and every one of its ligands, thereby preventing the generation of oxidative stress and activation of NF-κB regulated genes, such as the cytokines IL-1, and TNF-α. Thus, antagonizing the binding of physiological ligands to RAGE prevent targeted pathophysiological consequences and useful for management or treatment of diseases, i.e., AGE-RAGE interaction leading to diabetic complications, S100/EN-RAGE/calgranulin-RAGE interaction leading to inflammatory diseases, β-amyloid-RAGE interaction leading to Alzheimer's Disease, and amphoterin-RAGE interaction leading to cancer.

I. RAGE and the Complications of Diabetes

As noted above, the compounds of the present invention are useful in the treatment of the complications of diabetes. It has been shown that nonenzymatic glycoxidation of macromolecules ultimately resulting in the formation of advanced glycation endproducts (AGEs) is enhanced at sites of inflammation, in renal failure, in the presence of hyperglycemia and other conditions associated with systemic or local oxidant stress (Dyer, D., et al., *J. Clin. Invest.*, 91:2463–2469 (1993); Reddy, S., et al., *Biochem.*, 34:10872–10878 (1995); Dyer, D., et al., *J. Biol. Chem.*, 266:11654–11660 (1991); Degenhardt, T., et al., *Cell Mol. Biol.*, 44:1139–1145 (1998)). Accumulation of AGEs in the vasculature can occur focally, as in the joint amyloid composed of AGE-$β_2$-microglobulin found in patients with dialysis-related amyloidosis (Miyata, T., et al., *J. Clin. Invest.*, 92:1243–1252 (1993); Miyata, T., et al., *J. Clin. Invest.*, 98:1088–1094 (1996)), or generally, as exemplified by the vasculature and tissues of patients with diabetes (Schmidt, A-M., et al., *Nature Med.*, 1:1002–1004 (1995)). The progressive accumulation of AGEs over time in patients with diabetes suggests that endogenous clearance mechanisms are not able to function effectively at sites of AGE deposition. Such accumulated AGEs have the capacity to alter cellular properties by a number of mechanisms. Although RAGE is expressed at low levels in normal tissues and vasculature, in an environment where the receptor's ligands accumulate, it has been shown that RAGE becomes upregulated (Li, J. et al., *J. Biol. Chem.*, 272:16498–16506 (1997); Li, J., et al., *J. Biol. Chem.*, 273:30870–30878 (1998); Tanaka, N., et al., *J. Biol. Chem,.* 275:25781–25790 (2000)). RAGE expression is increased in endothelium, smooth muscle cells and infiltrating mononuclear phagocytes in diabetic vasculature. Also, studies in cell culture have demonstrated that AGE-RAGE interaction caused changes in cellular properties important in vascular homeostasis.

II. RAGE and Cellular Dysfunction in the Amyloidoses

Also as noted above, the compounds of the present invention are useful in treating amyloidoses and Alzheimer's disease. RAGE appears to be a cell surface receptor which binds β-sheet fibrillar material regardless of the composition of the subunits (amyloid-β peptide, Aβ, amylin, serum amyloid A, prion-derived peptide) (Yan, S. -D., et al., *Nature*, 382:685–691 (1996); Yan, S-D., et al., *Nat. Med.*, 6:643–651 (2000)). Deposition of amyloid has been shown to result in enhanced expression of RAGE. For example, in the brains of patients with Alzheimer's disease (AD), RAGE expression increases in neurons and glia (Yan, S. -D., et al., *Nature* 382:685–691 (1996)). The consequences of Aβ interaction with RAGE appear to be quite different on neurons versus microglia. Whereas microglia become activated as a consequence of Aβ-RAGE interaction, as reflected by increased motility and expression of cytokines, early RAGE-mediated neuronal activation is superceded by cytotoxicity at later times. Further evidence of a role for RAGE in cellular interactions of Aβ concerns inhibition of Aβ-induced cerebral vasoconstriction and transfer of the peptide across the blood-brain barrier to brain parenchyma when the receptor was blocked (Kumar, S., et al., *Neurosci. Program*, p 141-#275.19 (2000)). Inhibition of RAGE-amyloid interaction has been shown to decrease expression of cellular RAGE and cell stress markers (as well as NF-κB activation), and diminish amyloid deposition (Yan, S-D., et al., *Nat. Med.*, 6:643–651 (2000)) suggesting a role for RAGE-amyloid interaction in both perturbation of cellular properties in an environment enriched for amyloid (even at early stages) as well as in amyloid accumulation.

III. RAGE and Propagation of the Immune/Inflammatory Response

As noted above, the compounds of the present invention are useful in treating inflammation. For example, S100/calgranulins have been shown to comprise a family of closely related calcium-binding polypeptides characterized by two EF-hand regions linked by a connecting peptide (Schafer, B. et al., *TIBS*, 21:134–140 (1996); Zimmer, D., et al., *Brain Res. Bull.*, 37:417–429 (1995); Rammes, A., et al., *J. Biol. Chem.*, 272:9496–9502 (1997); Lugering, N., et al., *Eur. J Clin. Invest.*, 25:659–664 (1995)). Although they lack signal peptides, it has long been known that S100/calgranulins gain access to the extracellular space, especially at sites of chronic immune/inflammatory responses, as in cystic fibrosis and rheumatoid arthritis. RAGE is a receptor for many members of the S100/calgranulin family, mediating their proinflammatory effects on cells such as lymphocytes and mononuclear phagocytes. Also, studies on delayed-type hypersensitivity response, colitis in IL-10 null mice, collagen-induced arthritis, and experimental autoimmune encephalitis models suggest that RAGE-ligand interaction (presumably with S100/calgranulins) has a proximal role in the inflammatory cascade.

IV. RAGE and Amphoterin

As noted above, the compounds of the present invention are useful in treating tumor and tumor metastasis. For example, amphoterin is a high mobility group I nonhistone chromosomal DNA binding protein (Rauvala, H., et al., *J. Biol. Chem.*, 262:16625–16635 (1987); Parkikinen, J., et al., *J. Biol. Chem.* 268:19726–19738 (1993)) which has been shown to interact with RAGE. It has been shown that amphoterin promotes neurite outgrowth, as well as serving as a surface for assembly of protease complexes in the fibrinolytic system (also known to contribute to cell mobility). In addition, a local tumor growth inhibitory effect of blocking RAGE has been observed in a primary tumor model (C6 glioma), the Lewis lung metastasis model (Taguchi, A., et al., *Nature* 405:354–360 (2000)), and spontaneously arising papillomas in mice expressing the v-Ha-ras transgene (Leder, A., et al., *Proc. Natl. Acad. Sci.*, 87:9178–9182 (1990)).

Amphoterin is a high mobility group I nonhistone chromosomal DNA binding protein (Rauvala, H. and R. Pihlaskari. 1987. Isolation and some characteristics of an adhesive factor of brain that enhances neurite outgrowth in central neurons. *J. Biol. Chem.* 262:16625–16635. (Parkikinen, J., E. Raulo, J. Merenmies, R. Nolo, E. Kajander, M. Baumann, and H. Rauvala. 1993. Amphoterin, the 30 kDa protein in a family of HIMG1-type polypeptides. *J. Biol. Chem.* 268:19 726–19738).

V. RAGE and Erectile Dysfunction

Relaxation of the smooth muscle cells in the cavernosal arterioles and sinuses results in increased blood flow into the penis, raising corpus cavernosum pressure to culminate in penile erection. Nitric oxide is considered the principle stimulator of cavemosal smooth muscle relaxation (See Wingard C J, Clinton W, Branam H, Stopper V S, Lewis R W, Mills T M, Chitaley K. Antagonism of Rho-kinase stimulates rat penile erection via a nitric oxide-independent pathway. Nature Medicine 2001 January; 7(1):119–122). RAGE activation produces oxidants (See Yan, S-D., Schmidt A-M., Anderson, G., Zhang, J., Brett, J., Zou, Y-S., Pinsky, D., and Stem, D. Enhanced cellular oxidant stress by the interaction of advanced glycation endproducts with their receptors/binding proteins. J. Biol. Chem. 269:9889–9887, 1994.) via an NADH oxidase-like enzyme, therefore suppressing the circulation of nitric oxide. Potentially by inhibiting the activation of RAGE signaling pathways by decreasing the intracellular production of AGEs, generation of oxidants will be attenuated. RAGE blockers may promote and facilitate penile erection by blocking the access of ligands to RAGE.

The calcium-sensitizing Rho-kinase pathway may play a synergistic role in cavernosal vasoconstriction to maintain penile flaccidity. The antagonism of Rho-kinase results in increased corpus cavernosum pressure, initiating the erectile response independently of nitric oxide (Wingard et al.). One of the signaling mechanisms activated by RAGE involves the Rho-kinase family such as cdc42 and rac (See Huttunen H J, Fages C, Rauvala H. Receptor for advanced glycation end products (RAGE)-mediated neurite outgrowth and activation of NF-kappaB require the cytoplasmic domain of the receptor but different downstream signaling pathways. J Biol Chem Jul. 9, 1999 ;274(28):19919–24). Thus, inhibiting activation of Rho-kinases via suppression of RAGE signaling pathways will enhance and stimulate penile erection independently of nitric oxide.

Thus, in a further aspect, the present invention provides a method for the inhibition of the interaction of RAGE with physiological ligands. In a preferred embodiment of this aspect, the present invention provides a method for treating a disease state selected from the group consisting of acute and chronic inflammation, symptoms of diabetes, vascular permeability, nephropathy, atherosclerosis, retinopathy, Alzheimer's disease, erectile dysfunction, and tumor invasion and/or metastasis, which comprises administering to a subject in need thereof a compound of the present invention, preferably a pharmacologically effective amount, more preferably a therapeutically effective amount. In a preferred embodiment, at least one compound of Formula (I) is utilized, either alone or in combination with one or more known therapeutic agents. In a further preferred embodiment, the present invention provides method of prevention and/or treatment of RAGE mediated human diseases, treatment comprising alleviation of one or more symptoms resulting from that disorder, to an outright cure for that particular disorder or prevention of the onset of the disorder, the method comprising administration to a human in need thereof a therapeutically effective amount of a compound of the present invention, preferably a compound of Formula (I).

In this method, factors which will influence what constitutes an effective amount will depend upon the size and weight of the subject, the biodegradability of the therapeutic agent, the activity of the therapeutic agent, as well as its bioavailability. As used herein, the phrase "a subject in need thereof" includes mammalian subjects, preferably humans, who either suffer from one or more of the aforesaid diseases or disease states or are at risk for such. Accordingly, in the context of the therapeutic method of the invention, this method also is comprised of a method for treating a mammalian subject prophylactically, or prior to the onset of diagnosis such disease(s) or disease state(s).

In a further aspect of the present invention, the RAGE modulators of the invention are utilized in adjuvant therapeutic or combination therapeutic treatments with other known therapeutic agents.

The term "treatment" as used herein, refers to the full spectrum of treatments for a given disorder from which the patient is suffering, including alleviation of one, most of all symptoms resulting from that disorder, to an outright cure for the particular disorder or prevention of the onset of the disorder.

The following is a non-exhaustive listing of adjuvants and additional therapeutic agents which may be utilized in combination with the RAGE modulators of the present invention:

Pharmacologic classifications of anticancer agents:
1. Alkylating agents: Cyclophosphamide, nitrosoureas, carboplatin, cisplatin, procarbazine
2. Antibiotics: Bleomycin, Daunorubicin, Doxorubicin
3. Antimetabolites: Methotrexate, Cytarabine, Fluorouracil
4. Plant alkaloids: Vinblastine, Vincristine, Etoposide, Paclitaxel,
5. Hormones: Tamoxifen, Octreotide acetate, Finasteride, Flutamide
6. Biologic response modifiers: Interferons, Interleukins, Pharmacologic classifications of treatment for Rheumatoid Arthritis (Inflammation)
1. Analgesics: Aspirin
2. NSAIDs (Nonsteroidal anti-inflammatory drugs): Ibuprofen, Naproxen, Diclofenac
3. DMARDs (Disease-Modifying Antirheumatic drugs): Methotrexate, gold preparations, hydroxychloroquine, sulfasalazine
4. Biologic Response Modifiers, DMARDs: Etanercept, Infliximab Glucocorticoids Pharmacologic classifications of treatment for Diabetes Mellitus
1. Sulfonylureas: Tolbutamide, Tolazamide, Glyburide, Glipizide
2. Biguanides: Metformin
3. Miscellaneous oral agents: Acarbose, Troglitazone
4. Insulin Pharmacologic classifications of treatment for Alzheimer's Disease

| | | |
|---|---|---|
| 1. | Cholinesterase Inhibitor: | Tacrine, Donepezil |
| 2. | Antipsychotics: | Haloperidol, Thioridazine |
| 3. | Antidepressants: | Desipramine, Fluoxetine, Trazodone, Paroxetine |
| 4. | Anticonvulsants: | Carbamazepine, Valproic acid |

In a further preferred embodiment, the present invention provides a method of treating RAGE mediated diseases, the method comprising administering to a subject in need thereof, a therapeutically effective amount of a compound of Formula (I) in combination with therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants. In a further preferred embodiment, the present invention provides the pharmaceutical composition of the invention as described above, further comprising one or more therapeutic agents selected from the group consisting of alkylating agents, antimetabolites, plant alkaloids, antibiotics, hormones, biologic response modifiers, analgesics, NSAIDs, DMARDs, glucocorticoids, sulfonylureas, biguanides, insulin, cholinesterase inhibitors, antipsychotics, antidepressants, and anticonvulsants.

Generally speaking, the compound of the present invention, preferably Formula (I), is administered at a dosage level of from about 0.01 to 500 mg/kg of the body weight of the subject being treated, with a preferred dosage range between 0.01 and 200 mg/kg, most preferably 0.1 to 100 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 50 mg of active ingredient. This dosage has to be individualized by the clinician based on the specific clinical condition of the subject being treated. Thus, it will be understood that the specific dosage level for any particular patient will depend upon a variety of factors including the activity of the specific compound employed, the age, body weight, general health, sex, diet, time of administration, route of administration, rate of excretion, drug combination and the severity of the particular disease undergoing therapy.

While the invention has been described and illustrated with reference to certain preferred embodiments therof, those skilled in the art will appreciate that various changes, modifications and substitutions can be made therein without departing from the spirit and scope of the invention. For example, effective dosages other than the preferred dosages as set forth herein may be applicable as a consequence of variations in the responsiveness of the mammal being treated for RAGE-mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:

1. A compound comprising at least one moiety of the formula

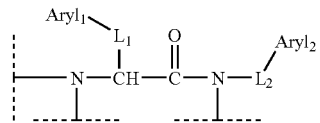

wherein $L_1$ is a $C_1$–$C_4$ alkyl group and $L_2$ is a direct bond, and $Aryl_1$ and $Aryl_2$ are aryl, wherein each of $Aryl_1$ and $Aryl_2$ are substituted by at least one lipophilic group selected from the group consisting of a) —Y—$C_{16}$ alkyl;
b) —Y-aryl;
c) —Y—$C_{1-6}$ alkylaryl;
d) —Y—$C_{1-6}$-alkyl-$NR_7R_8$;
e) —Y—$C_{1-6}$-alkyl-W—$R_{20}$;
wherein
Y and W are, independently selected from the group consisting of —$CH_2$—, —O—, —N(H), —S—, $SO_2$—, —CON(H)—, —NHC(O)—, —NHCON(H)—, —$NHSO_2$—, —$SO_2$N(H)—, —C(O)—O—, —$NHSO_2$NH—, —O—CO—,

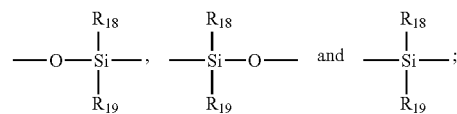

and f) halogen, hydroxyl, cyano, carbamoyl, and carboxyl;
wherein
$R_{18}$ and $R_{19}$ are independently selected from the group consisting of aryl, $C_1$–$C_6$ alkyl, $C_1$–$C_6$ alkylaryl, $C_1$–$C_6$ alkoxy, and $C_1$–$C_6$ alkoxyaryl;
$R_{20}$ is selected from the group consisting of aryl, $C_1$–$C_6$ alkyl, and $C_1$–$C_6$ alkylaryl;
$R_7$, $R_8$, $R_9$ and $R_{10}$ are independently selected from the group consisting of hydrogen, aryl, $C_1$–$C_6$ alkyl, and $C_1$–$C_6$ alkylaryl; and wherein $R_7$ and $R_8$ may be taken together to form a ring having the formula —$(CH_2)_m$—X—$(CH_2)_n$— bonded to the nitrogen atom to which $R_7$ and $R_8$ are attached, wherein m and n are, independently, 1, 2, 3, or 4; X is selected from the group consisting of —$CH_2$—, —O—, —S—, —$S(O_2)$—, —C(O)—, —CON(H)—, —NHC(O)—, —NHCON(H)—, —$NHSO_2$—, —$SO_2$N(H)—, —C(O)—O—, —O—C(O)—, —$NHSO_2$NH—,

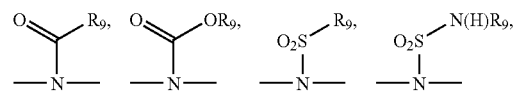

-continued

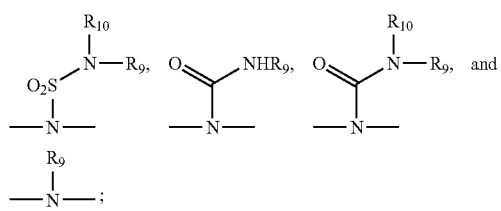

or a pharmaceutically acceptable salt thereof,
wherein at least one of $Aryl_1$ and $Aryl_2$ is substituted with a lipophilic group of the formula —Y—$C_{1-6}$-alkyl-$NR_7R_8$.

2. The compound of claim 1, wherein at least one of $Aryl_1$ or $Aryl_2$ is further substituted with a lipophilic group selected from the group consisting of $C_1$–$C_6$ alkyl, $C_1$–$C_6$ alkoxy, $C_1$–$C_6$ alkylaryl, and $C_1$–$C_6$ alkoxyaryl.

3. A pharmaceutical composition comprising a compound of claim 1 together with one or more pharmaceutically acceptable carriers or diluents.

4. The pharmaceutical composition of to claim 3, in the form of an oral dosage or parenteral dosage unit.

5. The pharmaceutical composition of claim 3, wherein said compound is administered as a dose in a range from about 0.01 to 500 mg/kg of body weight per day.

6. The pharmaceutical composition of claim 3, wherein said compound is administered as a dose in a range from about 0.1 to 200 mg/kg of body weight per day.

7. The pharmaceutical composition of claim 3, wherein said compound is administered as a dose in a range from about 0.1 to 100 mg/kg of body weight per day.

* * * * *

UNITED STATES PATENT AND TRADEMARK OFFICE
CERTIFICATE OF CORRECTION

PATENT NO. : 7,067,554 B2 Page 1 of 1
APPLICATION NO. : 10/611741
DATED : June 27, 2006
INVENTOR(S) : Adnan M.M. Mjalli et al.

It is certified that error appears in the above-identified patent and that said Letters Patent is hereby corrected as shown below:

At column 40, line 21, please change "a) $-Y-C_{16}$alkyl;" to recite --a) $-Y-C_{1-6}$alkyl;--

Signed and Sealed this

Third Day of February, 2009

JOHN DOLL
*Acting Director of the United States Patent and Trademark Office*